(12) United States Patent
Eastman et al.

(10) Patent No.: US 11,402,378 B2
(45) Date of Patent: Aug. 2, 2022

(54) BIOMARKERS AND METHODS FOR ASSESSING RESPONSE TO INFLAMMATORY DISEASE THERAPY

(71) Applicant: Laboratory Corporation of America Holdings, Burlington, NC (US)

(72) Inventors: Paul Scott Eastman, South San Francisco, CA (US); William Manning, South San Francisco, CA (US)

(73) Assignee: Laboratory Corporation of America Holdings, Burlington, NC (US)

( * ) Notice: Subject to any disclaimer, the term of this patent is extended or adjusted under 35 U.S.C. 154(b) by 176 days.

(21) Appl. No.: 16/164,297

(22) Filed: Oct. 18, 2018

(65) Prior Publication Data

US 2019/0049443 A1 Feb. 14, 2019

Related U.S. Application Data

(63) Continuation of application No. PCT/US2017/028356, filed on Apr. 19, 2017.

(60) Provisional application No. 62/324,968, filed on Apr. 20, 2016.

(51) Int. Cl.
*G01N 33/00* (2006.01)
*G01N 33/564* (2006.01)

(52) U.S. Cl.
CPC ..... *G01N 33/564* (2013.01); *G01N 2800/102* (2013.01); *G01N 2800/52* (2013.01)

(58) Field of Classification Search
CPC .. G01N 33/00; G01N 33/564; G01N 2800/52; G01N 2800/60; G01N 2800/102; G01N 2800/00; A61K 38/00
See application file for complete search history.

(56) References Cited

U.S. PATENT DOCUMENTS

| | | | |
|---|---|---|---|
| 4,230,797 A | 10/1980 | Boguslaski | |
| 4,233,402 A | 11/1980 | Maggio | |
| 4,275,149 A | 6/1981 | Litman | |
| 4,376,110 A | 3/1983 | David | |
| 4,659,678 A | 4/1987 | Forrest | |
| 4,727,022 A | 2/1988 | Skold | |
| 5,018,067 A | 5/1991 | Mohlenbrock | |
| 5,744,305 A | 4/1998 | Fodor | |
| 2002/0038227 A1 | 3/2002 | Fey | |
| 2003/0224386 A1 | 12/2003 | Guild | |
| 2004/0122296 A1 | 6/2004 | Hatlestad | |
| 2004/0122297 A1 | 6/2004 | Stahmann | |
| 2005/0142569 A1* | 6/2005 | Guild | G01N 33/564 435/6.11 |
| 2011/0137851 A1* | 6/2011 | Cavet | C12Q 1/6883 706/54 |

FOREIGN PATENT DOCUMENTS

| | | |
|---|---|---|
| WO | 2004056456 | 7/2004 |
| WO | 2004088309 | 10/2004 |
| WO | 2014057108 | 4/2014 |
| WO | 2015191423 | 12/2015 |

OTHER PUBLICATIONS

Ha et al., Joint Bone Spine, 2014, 81:186-194.*
Burska et al., Mediators of Inflammation, vol. 2014, Article ID. 545493, 2014.
Choi et al., AB0193,Annal of the Rheumatic Diseases, vol. 72, p. A845, 2013.
Hirata et al., Rheumatology, vol. 52, pp. 1202-1207, 2013.
International Preliminary Report on Patentability from Application No. PCT/US2017/028356, dated Nov. 1, 2018, 11 pages.
International Search Report & Written Opinion from Application No. PCT/US2017/028356, dated Jul. 24, 2017, 15 pages.
Aletaha et al., Arth. Rheum. 2005, 52(9):2625-2636.
Baecklund et al., Arth. Rheum. 2006, 54(3):692-701.
Banerjee et al., Am. J. Cardiol. 2008, 101(8):1201-1205.
Breedveld et al., Arth. Rheum. 2006, 54(1):26-37.
Breiman and JH Friedman, J. Royal. Stat. Soc. B 1997, 59(1):3-54.
Brown et al., Arth. Rheum. 2006, 54:3761-3773.
Brown et al., Arth. Rheum. 2008, 58(10):2958-2967.
Churchman et al., Ann. Rheum. Dis. 2009, 68:A1-A56, Abstract A77.
Cohen et al., Ann. Rheum. Dis. 2007, 66:358-363.
Felson et al., Arth. Rheum. 1993, 36(6):729-740.
Felson et al., Arth. Rheum. 1995, 38(6):727-735.
Goodson et al., Ann. Rheum. Dis. 2005, 64(11):1595-1601.
Gossec et al., Ann. Rheum. Dis. 2004, 63(6):675-680.
Kisner, "Product development: the making of the Abbott Architect," Clin. Lab. Manage. Rev. Nov.-Dec. 1997, 11(6):419-21.
Kroot et al., Arth. Rheum. 2000, 43(8):1831-1835.
Lipsky et al., N. Engl. J. Med. 2003, 343:1594-602.
Mäkinen et al., Ann. Rheum. Dis. 2005, 64(10):1410-1413.
Mallya et al., J. Rheum. 1982, 9(2):224-228.
Matucci-Cerinic, Clin. Exp. Rheum. 2002, 20(4):443-444.
Nadareishvili et al., Arth. Rheum. 2008, 59(8):1090-1096.
Nell et al., Lancet 2005, 365(9455):199-200.
Ognibene et al., "A new modular chemiluminescence immunoassay analyzer evaluated," Clin. Chem. Lab. Med. Mar. 2000, 38(3):251-60.
Park et al., "Three-year experience in using total laboratory automation system," Southeast Asian J. Trop. Med. Public Health 2002, 33 Suppl 2:68-73.
Pauli et al., "The Abbott Architect c8000: analytical performance and productivity characteristics of a new analyzer applied to general chemistry testing," Clin. Lab. 2005, 51(1-2):31-41.

(Continued)

Primary Examiner — Xiaozhen Xie
(74) Attorney, Agent, or Firm — Kilpatrick Townsend & Stockton LLP

(57) ABSTRACT

Provided herein are methods for assessing response to inflammatory disease therapy. The methods include performing immunoassays to generate scores based on quantitative data for expression of biomarkers relating to inflammatory biomarkers to assess disease activity in inflammatory diseases, e.g., rheumatoid arthritis. Also provided are uses of inflammatory biomarkers for guiding treatment decisions.

7 Claims, 2 Drawing Sheets

(56) References Cited

OTHER PUBLICATIONS

Pearson et al., Circulation 2003, 107(3):499-511.
Pettit et al., Am. J. Pathol. 2001, 159:1689-99.
Pincus et al., Clin. Exp. Rheum. 2004, 22(Suppl. 35):S50-S56.
Plant et al., Arth. Rheum. 2000, 43(7):1473-1477.
Prevoo et al., Arth. Rheum. 1995, 38(1):44-48.
Ridker et al., NEJM 2000, 342(12):836-843.
Smolen et al., Arth. Rheum. 2005, 52(4):1020-30.
Smolen et al., Rheumatology (Oxford) 2003, 42:244-257.
Stucki et al., Arth. Rheum. 1995, 38(6):795-798.
Van den Berg et al., Arth. Rheum. 2005, 52:995-999.
Van der Heijde et al., Ann. Rheum. Dis. 1990, 49(11):916-920.
Van Gestel et al., Arth. Rheum. 1998, 41(10):1845-1850.
Van Leeuwen et al., Br. J. Rheum. 1993, 32(suppl.):9-13.
Vasan, Circulation 2006, 113(19):2335-2362.
Weinblatt et al., N. Engl. J. Med. 1999, 340:253-25.
Wilson et al., "Clinical Chemistry Analyzer Sub-System Level Performance," American Association for Clinical Chemistry Annual Meeting, Chicago, Ill., Jul. 23-27, 2006.
Wirth et al., Proteomics 2002, 2(10):1445-1451.
Wolfe, Arth. Rheum. 2000, 43(12):2751-2761.
Wolfe, J. Rheum. 1997, 24:1477-1485.
Zatarain and V. Strand, Nat. Clin. Pract. Rheum. 2006, 2(11):611-618 (Review).
Khan, Muhammad, "Spondyloarthropathies: Treatment Advances from ACR 2008", Medscape.org, Dec. 10, 2008.

\* cited by examiner

BIOMARKERS AND METHODS FOR ASSESSING RESPONSE TO INFLAMMATORY DISEASE THERAPY

This application claims priority to International application number PCT/US2017/028356, filed Apr. 19, 2017, which claims priority benefit to U.S. provisional patent application No. 62/324,968, filed Apr. 20, 2016, the entire contents of which are hereby incorporated by reference.

BACKGROUND

This application is directed to the fields of bioinformatics and inflammatory and autoimmune diseases, with methods of assessing response to inflammatory disease therapy. Rheumatoid arthritis ("RA") is an example of an inflammatory disease, and is a chronic, systemic autoimmune disorder. It is one of the most common systemic autoimmune diseases worldwide. The immune system of the RA subject targets the subject's joints as well as other organs including the lung, blood vessels and pericardium, leading to inflammation of the joints (arthritis), widespread endothelial inflammation, and even destruction of joint tissue. Erosions and joint space narrowing are largely irreversible and result in cumulative disability.

The precise etiology of RA has not been established, but underlying disease pathogenesis is multifactorial and includes inflammation and immune dysregulation. The precise mechanisms involved are different in individual subjects, and can change in those subjects over time. Variables such as race, sex, genetics, hormones, and environmental factors can impact the development and severity of RA disease. Emerging data are also beginning to reveal the characteristics of new RA subject subgroups and complex overlapping relationships with other autoimmune disorders. Disease duration and level of inflammatory activity is also associated with other comorbidities such as risk of lymphoma, extra-articular manifestations, and cardiovascular disease. See, e.g., S. Banerjee et al., *Am. J. Cardiol.* 2008, 101(8):1201-1205; E. Baecklund et al., *Arth. Rheum.* 2006, 54(3):692-701; and, N. Goodson et al., *Ann. Rheum. Dis.* 2005, 64(11):1595-1601.

Traditional models for treating RA are based on the expectation that controlling disease activity (e.g., inflammation) in an RA subject should slow down or prevent disease progression, in terms of radiographic progression, tissue destruction, cartilage loss and joint erosion. There is evidence, however, that disease activity and disease progression can be uncoupled, and may not always function completely in tandem. Indeed, different cell signaling pathways and mediators are involved in these two processes. See W. van den Berg et al., *Arth. Rheum.* 2005, 52:995-999. The uncoupling of disease progression and disease activity is described in a number of RA clinical trials and animal studies. See, e.g., P E Lipsky et al., *N. Engl. J. Med.* 2003, 343:1594-602.; A K Brown et al., *Arth. Rheum.* 2006, 54:3761-3773; and, A R Pettit et al., *Am. J. Pathol.* 2001, 159:1689-99. Studies of RA subjects indicate limited association between clinical and radiographic responses. See E. Zatarain and V. Strand, *Nat. Clin. Pract. Rheum.* 2006, 2(11):611-618 (Review). RA subjects have been described who demonstrated radiographic benefits from combination treatment with infliximab and methotrexate (MTX), yet did not demonstrate any clinical improvement, as measured by DAS (Disease Activity Score) and CRP (C-reactive protein). See J S Smolen et al., *Arth. Rheum.* 2005, 52(4):1020-30. To track the uncoupling of disease activity and remission, and to analyze the relationship between disease activity, treatment, and progression, RA subjects should be assessed frequently for both disease activity and progression during therapy. Recent advances in assessing inflammatory disease activity and progression are described in US 2011/0137851, which is hereby incorporated by reference in its entirety.

There is a need to classify subjects by disease activity in order to ensure that each receives treatment that is appropriate and optimized for that patient. In treatment for RA, for example, the use of disease-modifying anti-rheumatic drug (DMARD) combinations has become accepted for subjects who fail to respond to a single DMARD. Studies analyzing treatment with MTX alone and treatment with MTX in combination with other DMARDs demonstrate that in DMARD-naive subjects, the balance of efficacy versus toxicity favors MTX monotherapy, while in DMARD-inadequate responders, the evidence is inconclusive. In regards to biologics (e.g., anti-TNFα), studies support the use of biologics in combination with MTX in subjects with early RA (eRA), or in subjects with established RA who have not yet been treated with MTX. For patients with eRA, MTX is recommended as first-line treatment and in non-responders both the addition of conventional non-biological disease modifying anti-rheumatic drug therapy (triple DMARD therapy) and of biological (e.g., anti-TNF) therapy are known in the art. The number of drugs available for treating RA is increasing; from this it follows that the number of possible combinations of these drugs is increasing as well. In addition, the chronological order in which each drug in a combination is administered can be varied depending on the needs of the subject. For the clinician to apply a simple trial-and-error process to find the optimum treatment for the RA subject from among the myriad of possible combinations, the clinician runs the risk of under- or over treating the subject. Irreversible joint damage for the subject could be the result. See, e.g., A K Brown et al., *Arth. Rheum.* 2008, 58(10):2958-2967, and G. Cohen et al., *Ann. Rheum. Dis.* 2007, 66:358-363. Clearly there exists a need to accurately classify subjects by disease activity, in order to establish their optimal treatment regimen.

Current clinical management and treatment goals, in the case of RA, focus on the suppression of disease activity with the goal of improving the subject's functional ability and slowing the progression of joint damage. Clinical assessments of RA disease activity include measuring the subject's difficulty in performing activities, morning stiffness, pain, inflammation, and number of tender and swollen joints, an overall assessment of the subject by the physician, an assessment by the subject of how good s/he feels in general, and measuring the subject's erythrocyte sedimentation rate (ESR) and levels of acute phase reactants, such as CRP. Composite indices comprising multiple variables, such as those just described, have been developed as clinical assessment tools to monitor disease activity. The most commonly used are: American College of Rheumatology (ACR) criteria (D T Felson et al., *Arth. Rheum.* 1993, 36(6):729-740 and D T Felson et al., *Arth. Rheum.* 1995, 38(6):727-735); Clinical Disease Activity Index (CDAI) (D. Aletaha et al., *Arth. Rheum.* 2005, 52(9):2625-2636); the DAS (M L L Prevoo et al., *Arth. Rheum.* 1995, 38(1):44-48 and A M van Gestel et al., *Arth. Rheum.* 1998, 41(10):1845-1850); Rheumatoid Arthritis Disease Activity Index (RADAI) (G. Stucki et al., *Arth. Rheum.* 1995, 38(6):795-798); and, Simplified Disease Activity Index (SDAI) (J S Smolen et al., *Rheumatology* (Oxford) 2003, 42:244-257).

Current laboratory tests routinely used to monitor disease activity in RA subjects, such as CRP and ESR, are relatively non-specific (e.g., are not RA-specific and cannot be used to diagnose RA), and cannot be used to determine response to treatment or predict future outcomes. See, e.g., L. Gossec et al., *Ann. Rheum. Dis.* 2004, 63(6):675-680; E J A Kroot et al., *Arth. Rheum.* 2000, 43(8):1831-1835; H. Makinen et al., *Ann. Rheum. Dis.* 2005, 64(10):1410-1413; Z. Nadareishvili et al., *Arth. Rheum.* 2008, 59(8):1090-1096; N A Khan et al., Abstract, *ACR/ARHP Scientific Meeting* 2008; T A Pearson et al., *Circulation* 2003, 107(3):499-511; M J Plant et al., *Arth. Rheum.* 2000, 43(7):1473-1477; T. Pincus et al., *Clin. Exp. Rheum.* 2004, 22 (Suppl. 35):S50-S56; and, P M Ridker et al., *NEJM* 2000, 342(12):836-843. In the case of ESR and CRP, RA subjects may continue to have elevated ESR or CRP levels despite being in clinical remission (and non-RA subjects may display elevated ESR or CRP levels). Some subjects in clinical remission, as determined by DAS, continue to demonstrate continued disease progression radiographically, by erosion. Furthermore, some subjects who do not demonstrate clinical benefits still demonstrate radiographic benefits from treatment. See, e.g., F C Breedveld et al., *Arth. Rheum.* 2006, 54(1):26-37. Clearly, in order to predict future outcome and treat the RA subject accordingly, there is a need for clinical assessment tools that accurately assess an RA subject's disease activity level and that act as predictors of future course of disease.

Clinical assessments of disease activity contain subjective measurements of RA, such as signs and symptoms, and subject-reported outcomes, all difficult to quantify consistently. In clinical trials, the DAS is generally used for assessing RA disease activity. The DAS is an index score of disease activity based in part on these subjective parameters. Besides its subjectivity component, another drawback to use of the DAS as a clinical assessment of RA disease activity is its invasiveness. The physical examination required to derive a subject's DAS can be painful, because it requires assessing the amount of tenderness and swelling in the subject's joints, as measured by the level of discomfort felt by the subject when pressure is applied to the joints. Assessing the factors involved in DAS scoring is also time-consuming. Furthermore, to accurately determine a subject's DAS requires a skilled assessor so as to minimize wide inter- and intra-operator variability. A method of clinically assessing disease activity is needed that is less invasive and time-consuming than DAS, and more consistent, objective and quantitative, while being specific to the disease assessed (such as RA).

Developing biomarker-based tests (e.g., measuring cytokines), e.g. specific to the clinical assessment of RA, has proved difficult in practice because of the complexity of RA biology—the various molecular pathways involved and the intersection of autoimmune dysregulation and inflammatory response. Adding to the difficulty of developing RA-specific biomarker-based tests are the technical challenges involved; e.g., the need to block non-specific matrix binding in serum or plasma samples, such as rheumatoid factor (RF) in the case of RA. The detection of cytokines using bead-based immunoassays, for example, is not reliable because of interference by RF; hence, RF-positive subjects cannot be tested for RA-related cytokines using this technology (and RF removal methods attempted did not significantly improve results). See S. Churchman et al., *Ann. Rheum. Dis.* 2009, 68:A1-A56, Abstract A77. Approximately 70% of RA subjects are RF-positive, so any biomarker-based test that cannot assess RF-positive patients is obviously of limited use.

To achieve the maximum therapeutic benefits for individual subjects, it is important to be able to specifically quantify and assess the subject's disease activity at any particular time, determine the effects of treatment on disease activity, and predict future outcomes. No existing single biomarker or multi-biomarker test produces results demonstrating a high association with level of RA disease activity. The embodiments of the present teachings identify multiple serum biomarkers for the accurate clinical assessment of disease activity in subjects with chronic inflammatory disease, such as RA, along with methods of their use.

SUMMARY

The present teachings relate to biomarkers associated with inflammatory disease, and with autoimmune disease, including RA, and methods of using the biomarkers to measure disease activity in a subject.

In one embodiment, a method for assessing rheumatoid arthritis (RA) disease activity in a subject is provided. The method comprises performing at least one immunoassay on a first blood sample from the first subject to generate a first dataset comprising protein level data for at least two protein markers, wherein the at least two protein markers comprise at least two markers selected from Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B (CSTB), Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony- Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1); and determining a RA disease activity score from the first dataset using an interpretation function, wherein said RA disease activity score provides a quantitative measure of RA disease activity in said first subject. In another embodiment, the at least two protein markers comprise at least two markers selected from CPSD, SAP, PEDF, C-Peptide, tPA, TIG2, or FAS. In another embodiment, the at least two protein markers comprise at least two markers selected from CPSD, A1M, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15. In another embodiment, the at least two protein markers comprise at least two markers selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15. In another embodiment, the at least two protein markers comprise at least two markers selected from CPSD, SAP, PEDF, C-peptide, tPA, TIG2, or FAS. In another embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In another embodiment, the at least one immunoassay comprises a multiplex assay. In another embodiment, the interpretation function is based on a predictive model. In another embodiment, the method further comprises receiving a second dataset associated with a second sample obtained from said first subject, wherein said first sample and said second sample are obtained from said first subject at different times; determining a second RA disease activity score from said second dataset using said interpretation function; and comparing said first RA disease activity score and said second disease activity score to determine a change in said RA disease activity scores, wherein said changes indicates a change in said RA disease activity in said first subject. In another embodiment, said change in said RA disease activity score indicates the presence, absence, or extent of the subject's response to a therapeutic regimen.

In an embodiment, a method for determining the presence or absence of rheumatoid arthritis (RA) in a subject is provided. The method comprises performing at least one immunoassay on a first blood sample from the first subject to generate a first dataset comprising protein level data for at least two protein markers, wherein the at least two protein markers comprise at least two markers selected from Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B (CSTB), Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1); determining a RA disease score from the first dataset using an interpretation function determining an aggregate RA disease score from subjects in a population wherein said subjects are negative for RA; comparing the RA disease score from the first dataset to the aggregate RA disease score; and determining a presence or absence of RA in said first subject based on said comparison. In another embodiment, the at least two protein markers comprise at least two markers selected from CPSD, SAP, PEDF, C-Peptide, tPA, TIG2, or FAS. In another embodiment, the at least two protein markers comprise at least two markers selected from CPSD, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15. In another embodiment, the at least two protein markers comprise at least two markers selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15. In another embodiment, the at least two protein markers comprise at least two markers selected from CPSD, SAP, PEDF, C-peptide, tPA, TIG2, or FAS. In another embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In another embodiment, the at least one immunoassay comprises a multiplex assay. In another embodiment, the interpretation function is based on a predictive model. In another embodiment, the method further comprises receiving a second dataset associated with a second sample obtained from said first subject, wherein said first sample and said second sample are obtained from said first subject at different times; determining a second RA activity score from said second dataset using said interpretation function; and comparing said first RA disease activity score and said second disease activity score to determine a change in said presence or absence of RA. In another embodiment, said change in said RA activity score indicates the presence, absence, or extent of the subject's response to a therapeutic regimen.

In an embodiment, a method predicting radiographic progression, flare, or joint damage in a subject with rheumatoid arthritis (RA) is provided. The method comprises performing at least one immunoassay on a first blood sample from the first subject to generate a first dataset comprising protein level data for at least two protein markers, wherein the at least two protein markers comprise at least two markers selected from Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B (CSTB), Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1); and determining a RA radiographic progression, flare, or joint damage score from the first dataset using an interpretation function, wherein said RA radiographic progression, flare, or joint damage score provides a quantitative measure of RA radiographic progression, flare, or joint damage in said first subject. In another embodiment, the at least two protein markers comprise at least two markers selected from CPSD, SAP, PEDF, C-Peptide, tPA, TIG2, or FAS. In another embodiment, the at least two protein markers comprise at least two markers selected from CPSD, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15. In another embodiment, the at least two protein markers comprise at least two markers selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15. In another embodiment, the at least two protein markers comprise at least two markers selected from CPSD, SAP, PEDF, C-peptide, tPA, TIG2, or FAS. In another embodiment, performance of the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In another embodiment, the at least one immunoassay comprises a multiplex assay. In another embodiment, the interpretation function is based on a predictive model. In another embodiment, the method further comprises receiving a second dataset associated with a second sample obtained from said first subject, wherein said first sample and said second sample are obtained from said first subject at different times; determining a second RA radiographic progression, flare, or joint damage score from said second dataset using said interpretation function; and comparing said first RA radiographic progression, flare, or joint damage score and said second RA radiographic progression, flare, or joint damage score to determine a change in said RA radiographic progression, flare, or joint damage scores, wherein said changes indicates a change in said RA radiographic progression, flare, or joint damage in said first subject. In another embodiment, said change in said RA radiographic progression, flare, or joint damage score indicates the presence, absence, or extent of the subject's response to a therapeutic regimen.

In an embodiment, a method for generating nucleic acid and/or protein level data for a first subject is provided. The method comprises performing at least one immunoassay on a first blood sample from the first subject to generate a first dataset comprising protein level data for at least two protein markers, wherein the at least two protein markers comprise at least two markers selected from Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B (CSTB), Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1) wherein the first subject has rheumatoid arthritis (RA) or is suspected of having RA. In another embodiment, the at least two protein markers comprise at least two markers selected from CPSD, SAP, PEDF, C-Peptide, tPA, TIG2, or FAS. In another embodiment, the at least two protein markers comprise at least two markers selected from CPSD, A1M, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15. In another embodiment, the at least two protein markers comprise at least two markers selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15. In another embodiment, the at least two protein markers comprise at least two markers selected from CPSD, SAP, PEDF, C-peptide, tPA, TIG2, or FAS. In another embodiment, the at least one immunoassay comprises: obtaining the first blood sample, wherein the first blood sample comprises the protein markers; contacting the first blood sample with a plurality of distinct reagents; generating a plurality of distinct complexes between the reagents and markers; and detecting the complexes to generate the data. In another embodiment, the at least one immunoassay comprises a multiplex assay.

BRIEF DESCRIPTION OF THE DRAWINGS

The skilled artisan will understand that the drawings, described below, are for illustration purposes only. The drawings are not intended to limit the scope of the present teachings in any way.

DESCRIPTION OF VARIOUS EMBODIMENTS

Figure 1:
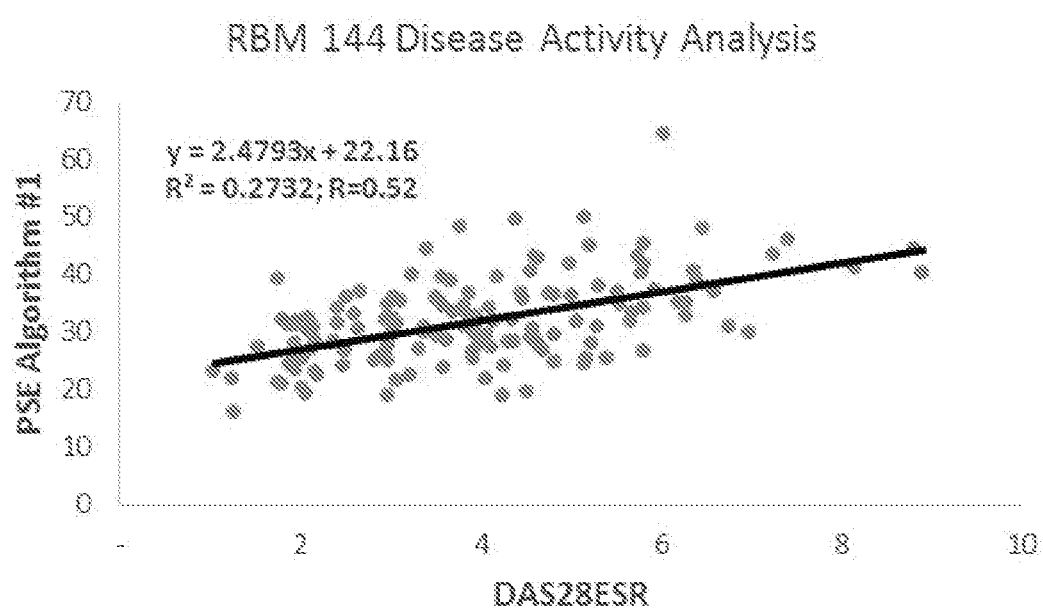
FIG. 1 illustrates a comparison of the biomarkers described herein to DAS28ESR.

These and other features of the present teachings will become more apparent from the description herein. While the present teachings are described in conjunction with various embodiments, it is not intended that the present teachings be limited to such embodiments. On the contrary, the present teachings encompass various alternatives, modifications, and equivalents, as will be appreciated by those of skill in the art.

The present teachings relate generally to the identification of biomarkers associated with subjects having inflammatory and/or autoimmune diseases, for example RA, and that are useful in determining or assessing disease activity, and in particular, in response to inflammatory disease therapy for recommending optimal therapy.

Most of the words used in this specification have the meaning that would be attributed to those words by one skilled in the art. Words specifically defined in the specification have the meaning provided in the context of the present teachings as a whole, and as are typically understood by those skilled in the art. In the event that a conflict arises between an art-understood definition of a word or phrase and a definition of the word or phrase as specifically taught in this specification, the specification shall control. It must be noted that, as used in the specification and the appended claims, the singular forms "a," "an," and "the" include plural referents unless the context clearly dictates otherwise.

Definitions

"Accuracy" refers to the degree that a measured or calculated value conforms to its actual value. "Accuracy" in clinical testing relates to the proportion of actual outcomes (true positives or true negatives, wherein a subject is correctly classified as having disease or as healthy/normal, respectively) versus incorrectly classified outcomes (false positives or false negatives, wherein a subject is incorrectly classified as having disease or as healthy/normal, respectively). Other and/or equivalent terms for "accuracy" can include, for example, "sensitivity," "specificity," "positive predictive value (PPV)," "the AUC," "negative predictive value (NPV)," "likelihood," and "odds ratio." "Analytical accuracy," in the context of the present teachings, refers to the repeatability and predictability of the measurement process. Analytical accuracy can be summarized in such measurements as, e.g., coefficients of variation (CV), and tests of concordance and calibration of the same samples or controls at different times or with different assessors, users, equipment, and/or reagents. See, e.g., R. Vasan, *Circulation* 2006, 113(19):2335-2362 for a summary of considerations in evaluating new biomarkers.

The term "administering" as used herein refers to the placement of a composition into a subject by a method or route that results in at least partial localization of the composition at a desired site such that a desired effect is produced. Routes of administration include both local and systemic administration. Generally, local administration results in more of the composition being delivered to a specific location as compared to the entire body of the subject, whereas, systemic administration results in delivery to essentially the entire body of the subject.

The term "algorithm" encompasses any formula, model, mathematical equation, algorithmic, analytical or programmed process, or statistical technique or classification analysis that takes one or more inputs or parameters, whether continuous or categorical, and calculates an output value, index, index value or score. Examples of algorithms include but are not limited to ratios, sums, regression operators such as exponents or coefficients, biomarker value transformations and normalizations (including, without limitation, normalization schemes that are based on clinical parameters such as age, gender, ethnicity, etc.), rules and guidelines, statistical classification models, and neural networks trained on populations. Also of use in the context of biomarkers are linear and non-linear equations and statistical classification analyses to determine the relationship between (a) levels of biomarkers detected in a subject sample and (b) the level of the respective subject's disease activity.

The term "analyte" in the context of the present teachings can mean any substance to be measured, and can encompass biomarkers, markers, nucleic acids, electrolytes, metabolites, proteins, sugars, carbohydrates, fats, lipids, cytokines, chemokines, growth factors, proteins, peptides, nucleic acids, oligonucleotides, metabolites, mutations, variants, polymorphisms, modifications, fragments, subunits, degradation products and other elements. For simplicity, standard gene symbols may be used throughout to refer not only to genes but also gene products/proteins, rather than using the standard protein symbol; e.g., APOA1 as used herein can refer to the gene APOA1 and also the protein ApoAI. In general, hyphens are dropped from analyte names and symbols herein (IL-6=IL6).

To "analyze" includes determining a value or set of values associated with a sample by measurement of analyte levels in the sample. "Analyze" may further comprise and comparing the levels against constituent levels in a sample or set of samples from the same subject or other subject(s). The biomarkers of the present teachings can be analyzed by any of various conventional methods known in the art. Some such methods include but are not limited to: measuring serum protein or sugar or metabolite or other analyte level, measuring enzymatic activity, and measuring gene expression.

The term "antibody" refers to any immunoglobulin-like molecule that reversibly binds to another with the required selectivity. Thus, the term includes any such molecule that is capable of selectively binding to a biomarker of the present teachings. The term includes an immunoglobulin molecule capable of binding an epitope present on an antigen. The term is intended to encompass not only intact immunoglobulin molecules, such as monoclonal and polyclonal antibodies, but also antibody isotypes, recombinant antibodies, bi-specific antibodies, humanized antibodies, chimeric antibodies, anti-idiopathic (anti-ID) antibodies, single-chain antibodies, Fab fragments, F(ab') fragments, fusion protein antibody fragments, immunoglobulin fragments, $F_v$ fragments, single chain $F_v$ fragments, and chimeras comprising an immunoglobulin sequence and any modifications of the foregoing that comprise an antigen recognition site of the required selectivity.

"Autoimmune disease" encompasses any disease, as defined herein, resulting from an immune response against substances and tissues normally present in the body. Examples of suspected or known autoimmune diseases include rheumatoid arthritis, early rheumatoid arthritis, axial spondyloarthritis, juvenile idiopathic arthritis, seronegative spondyloarthropathies, ankylosing spondylitis, psoriatic arthritis, antiphospholipid antibody syndrome, autoimmune hepatitis, Behçet's disease, bullous pemphigoid, coeliac disease, Crohn's disease, dermatomyositis, Goodpasture's syndrome, Graves' disease, Hashimoto's disease, idiopathic thrombocytopenic purpura, IgA nephropathy, Kawasaki disease, systemic lupus erythematosus, mixed connective tissue disease, multiple sclerosis, myasthenia gravis, polymyositis, primary biliary cirrhosis, psoriasis, scleroderma, Sjögren's syndrome, ulcerative colitis, vasculitis, Wegener's granulomatosis, temporal arteritis, Takayasu's arteritis, Henoch-Schonlein purpura, leucocytoclastic vasculitis, polyarteritis nodosa, Churg-Strauss Syndrome, and mixed cryoglobulinemic vasculitis.

A "biologic" or "biotherapy" or "biopharmaceutical" is a pharmaceutical therapy product manufactured or extracted from a biological substance. A biologic can include vaccines, blood or blood components, allergenics, somatic cells, gene therapies, tissues, recombinant proteins, and living cells; and can be composed of sugars, proteins, nucleic acids, living cells or tissues, or combinations thereof. Examples of biologic drugs can include but are not limited to biological agents that target the tumor necrosis factor (TNF)-alpha molecules and the TNF inhibitors, such as infliximab, adalimumab, etanercept and golimumab. Other classes of biologic drugs include IL1 inhibitors such as anakinra, T-cell modulators such as abatacept, B-cell modulators such as rituximab, and IL6 inhibitors such as tocilizumab.

"Biomarker," "biomarkers," "marker" or "markers" in the context of the present teachings encompasses, without limitation, cytokines, chemokines, growth factors, proteins, peptides, nucleic acids, oligonucleotides, and metabolites, together with their related metabolites, mutations, isoforms, variants, polymorphisms, modifications, fragments, subunits, degradation products, elements, and other analytes or sample-derived measures. Biomarkers can also include mutated proteins, mutated nucleic acids, variations in copy numbers and/or transcript variants. Biomarkers also encompass non-blood borne factors and non-analyte physiological markers of health status, and/or other factors or markers not measured from samples (e.g., biological samples such as bodily fluids), such as clinical parameters and traditional factors for clinical assessments. Biomarkers can also include any indices that are calculated and/or created mathematically. Biomarkers can also include combinations of any one or more of the foregoing measurements, including temporal trends and differences. Where the biomarkers of certain embodiments of the present teachings are proteins, the gene symbols and names used herein are to be understood to refer to the protein products of these genes, and the protein products of these genes are intended to include any protein isoforms of these genes, whether or not such isoform sequences are specifically described herein. Where the biomarkers are nucleic acids, the gene symbols and names used herein are to refer to the nucleic acids (DNA or RNA) of these genes, and the nucleic acids of these genes are intended to include any transcript variants of these genes, whether or not such transcript variants are specifically described herein. Biomarkers can include, but are not limited to the biomarkers described in Tables 1-12 herein.

A "biomarker disease activity score," "BDAS score," or simply "BDAS," in the context of the present teachings, is a score that uses quantitative data to provide a quantitative measure of inflammatory disease activity or the state of inflammatory disease in a subject. A set of data from particularly selected biomarkers, such as from the disclosed set of biomarkers, is input into an interpretation function according to the present teachings to derive the BDAS score. The interpretation function, in some embodiments, can be created from predictive or multivariate modeling based on statistical algorithms. Input to the interpretation function can comprise the results of testing two or more of the disclosed set of biomarkers, alone or in combination with clinical parameters and/or clinical assessments, also described herein. In some embodiments of the present teachings, the BDAS score is a quantitative measure of autoimmune disease activity. In some embodiments, the BDAS score is a quantitative measure of RA disease activity.

A "clinical assessment," or "clinical datapoint" or "clinical endpoint," in the context of the present teachings can refer to a measure of disease activity or severity. A clinical assessment can include a score, a value, or a set of values that can be obtained from evaluation of a sample (or population of samples) from a subject or subjects under determined conditions. A clinical assessment can also be a questionnaire completed by a subject. A clinical assessment can also be predicted by biomarkers and/or other parameters. One of skill in the art will recognize that the clinical assessment for RA, as an example, can comprise, without limitation, one or more of the following: DAS (defined herein), DAS28, DAS28-ESR, DAS28-CRP, health assessment questionnaire (HAQ), modified HAQ (mHAQ), multi-dimensional HAQ (MDHAQ), visual analog scale (VAS), physician global assessment VAS, patient global assessment VAS, pain VAS, fatigue VAS, overall VAS, sleep VAS, simplified disease activity index (SDAI), clinical disease activity index (CDAI), routine assessment of patient index data (RAPID), RAPID3, RAPID4, RAPID5, American College of Rheumatology (ACR), ACR20, ACR50, ACR70, SF-36 (a well-validated measure of general health status), RA MM score (RAIVIRIS; or RA Mill scoring system), total Sharp score (TSS), van der Heijde-modified TSS, van der Heijde-modified Sharp score (or Sharp-van der Heijde score (SHS)), Larsen score, TJC, swollen joint count (SJC), CRP titer (or level), and erythrocyte sedimentation rate (ESR).

The term "clinical parameters" in the context of the present teachings encompasses all measures of the health status of a subject. A clinical parameter can be used to derive a clinical assessment of the subject's disease activity. Clinical parameters can include, without limitation: therapeutic regimen (including but not limited to DMARDs, whether conventional or biologics, steroids, etc.), TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, diastolic and systolic blood pressure, resting heart rate, height, weight, body-mass index, family history, CCP status (i.e., whether subject is positive or negative for anti-CCP antibody), CCP titer, RF status, RF titer, ESR, CRP titer, menopausal status, and whether a smoker/non-smoker.

"Clinical assessment" and "clinical parameter" are not mutually exclusive terms. There may be overlap in members of the two categories. For example, CRP concentration can be used as a clinical assessment of disease activity; or, it can be used as a measure of the health status of a subject, and thus serve as a clinical parameter.

Figure 2:
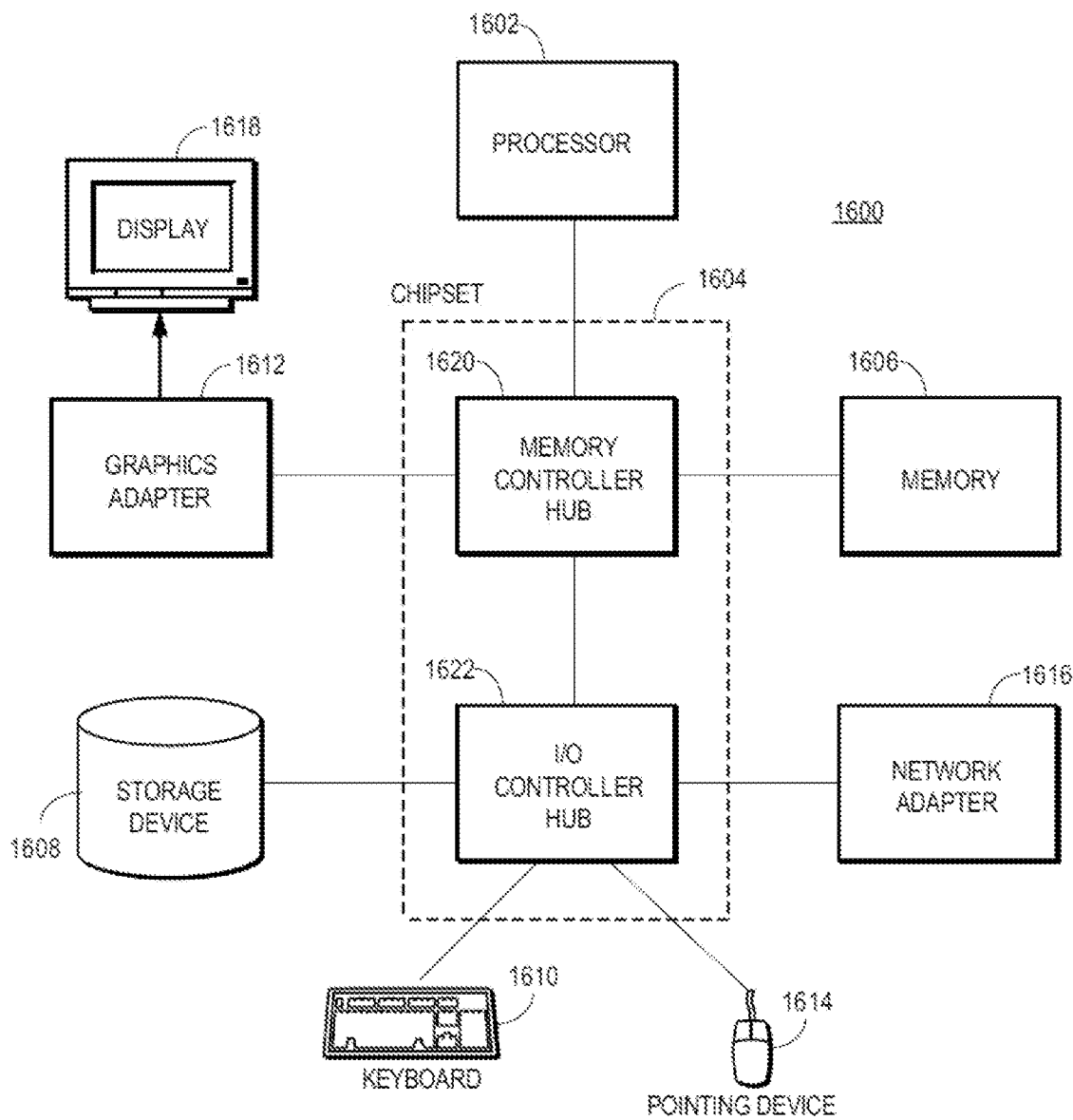
FIG. 2 illustrates a high-level block diagram of a computer (1600). Illustrated are at least one processor (1602) coupled to a chipset (1604). Also coupled to the chipset (1604) are a memory (1606), a storage device (1608), a keyboard (1610), a graphics adapter (1612), a pointing device (1614), and a network adapter (1616). A display (1618) is coupled to the graphics adapter (1612). In one embodiment, the functionality of the chipset (1604) is provided by a memory controller hub 1620) and an I/O controller hub (1622). In another embodiment, the memory (1606) is coupled directly to the processor (1602) instead of the chipset (1604). The storage device 1608 is any device capable of holding data, like a hard drive, compact disk read-only memory (CD-ROM), DVD, or a solid-state memory device. The memory (1606) holds instructions and data used by the processor (1602). The pointing device (1614) may be a mouse, track ball, or other type of pointing device, and is used in combination with the keyboard (1610) to input data into the computer system (1600). The graphics adapter (1612) displays images and other information on the display (1618). The network adapter (1616) couples the computer system (1600) to a local or wide area network.

The term "computer" carries the meaning that is generally known in the art; that is, a machine for manipulating data according to a set of instructions. For illustration purposes only, FIG. 2 is a high-level block diagram of a computer (1600). As is known in the art, a "computer" can have different and/or other components than those shown in FIG. 2. In addition, the computer 1600 can lack certain illustrated components. Moreover, the storage device (1608) can be local and/or remote from the computer (1600) (such as embodied within a storage area network (SAN)). As is known in the art, the computer (1600) is adapted to execute computer program modules for providing functionality described herein. As used herein, the term "module" refers to computer program logic utilized to provide the specified functionality. Thus, a module can be implemented in hardware, firmware, and/or software. In one embodiment, program modules are stored on the storage device (1608), loaded into the memory (1606), and executed by the processor (1602). Embodiments of the entities described herein can include other and/or different modules than the ones described here. In addition, the functionality attributed to the modules can be performed by other or different modules in other embodiments. Moreover, this description occasionally omits the term "module" for purposes of clarity and convenience.

The term "cytokine" in the present teachings refers to any substance secreted by specific cells that can be of the immune system that carries signals between cells and thus has an effect on other cells. The term "cytokines" encompasses "growth factors." "Chemokines" are also cytokines. They are a subset of cytokines that are able to induce chemotaxis in cells; thus, they are also known as "chemotactic cytokines."

"DAS" refers to the Disease Activity Score, a measure of the activity of RA in a subject, well-known to those of skill in the art. See D. van der Heijde et al., *Ann. Rheum. Dis.* 1990, 49(11):916-920. "DAS" as used herein refers to this particular Disease Activity Score. The "DAS28" involves the evaluation of 28 specific joints. It is a current standard well-recognized in research and clinical practice. Because the DAS28 is a well-recognized standard, it may be referred to as "DAS." Although "DAS" may refer to calculations based on 66/68 or 44 joint counts, unless otherwise specified, "DAS" herein will encompass the DAS28. Unless otherwise specified herein, the term "DAS28," as used in the present teachings, can refer to a DAS28-ESR or DAS28-CRP, as obtained by any of the four formulas described above; or, DAS28 can refer to another reliable DAS28 formula as may be known in the art.

A DAS28 can be calculated for an RA subject according to the standard as outlined at the das-score.nl website, maintained by the Department of Rheumatology of the University Medical Centre in Nijmegen, the Netherlands. The number of swollen joints, or swollen joint count out of a total of 28 (SJC28), and tender joints, or tender joint count out of a total of 28 (TJC28) in each subject is assessed. In some DAS28 calculations the subject's general health (GH) is also a factor, and can be measured on a 100 mm Visual Analogue Scale (VAS). GH may also be referred to herein as PG or PGA, for "patient global health assessment" (or merely "patient global assessment"). A "patient global health assessment VAS," then, is GH measured on a Visual Analogue Scale.

"DAS28-CRP" (or "DAS28CRP") is a DAS28 assessment calculated using CRP in place of ESR (see below). CRP is produced in the liver. Normally there is little or no CRP circulating in an individual's blood serum—CRP is generally present in the body during episodes of acute inflammation or infection, so that a high or increasing amount of CRP in blood serum can be associated with acute infection or inflammation. A blood serum level of CRP greater than 1 mg/dL is usually considered high. Most inflammation and infections result in CRP levels greater than 10 mg/dL. The amount of CRP in subject sera can be quantified using, for example, the DSL-10-42100 ACTIVE® US C-Reactive Protein Enzyme-Linked Immunosorbent Assay (ELISA), developed by Diagnostics Systems Laboratories, Inc. (Webster, Tex.). CRP production is associated with radiological progression in RA. See M. Van Leeuwen et al., *Br. J. Rheum.* 1993, 32 (suppl.):9-13). CRP is thus considered an appropriate alternative to ESR in measuring RA disease activity. See R. Mallya et al., *J. Rheum.* 1982, 9(2):224-228, and F. Wolfe, *J. Rheum.* 1997, 24:1477-1485.

The DAS28-CRP can be calculated according to either of the formulas below, with or without the GH factor, where "CRP" represents the amount of this protein present in a subject's blood serum in mg/L, "sqrt" represents the square root, and "ln" represents the natural logarithm:

DAS28-CRP with GH (or DAS28-CRP4)=(0.56*sqrt (TJC28)+0.28*sqrt(SJC28)+0.36*ln(CRP+1))+ (0.014*GH)+0.96; or, (a)

DAS28-CRP without GH (or DAS28-CRP3)= (0.56*sqrt(TJC28)+0.28*sqrt(SJC28)+0.36*ln (CRP+1))*1.10+1.15. (b)

The "DAS28-ESR" is a DAS28 assessment wherein the ESR for each subject is also measured (in mm/hour). The DAS28-ESR can be calculated according to the formula:

DAS28-ESR with GH (or DAS28-ESR4)=0.56*sqrt (TJC28)+0.28*sqrt(SJC28)+0.70*ln(ESR)+ 0.014*GH; or, (a)

DAS28-ESR without GH=0.56*sqrt(TJC28)+ 0.28*sqrt(SJC28)+0.70*ln(ESR)*1.08+0.16. (b)

A "dataset" is a set of numerical values resulting from evaluation of a sample (or population of samples) under a desired condition. The values of the dataset can be obtained, for example, by experimentally obtaining measures from a sample and constructing a dataset from these measurements; or alternatively, by obtaining a dataset from a service provider such as a laboratory, or from a database or a server on which the dataset has been stored.

A "difference" as used herein refers to an increase or decrease in the measurable expression of a biomarker or panel of biomarkers as compared to the measurable expression of the same biomarker or panel of biomarkers in a second samples.

The term "disease" in the context of the present teachings encompasses any disorder, condition, sickness, ailment, etc. that manifests in, e.g., a disordered or incorrectly functioning organ, part, structure, or system of the body, and results from, e.g., genetic or developmental errors, infection, poisons, nutritional deficiency or imbalance, toxicity, or unfavorable environmental factors.

A DMARD can be conventional or biologic. Examples of DMARDs that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Examples of other conventional DMARDs include, but are not limited to, folinic acid, D-pencillamine, gold auranofin, gold aurothioglucose, gold thiomalate, cyclophosphamide, and chlorambucil. Examples of biologic DMARDs (or biologic drugs) include but are not limited to biological agents that target the tumor necrosis factor (TNF)-alpha molecules such as infliximab, adalimumab, etanercept and golimumab. Other classes of biologic DMARDs include IL1 inhibitors such as anakinra, T-cell modulators such as abatacept, B-cell modulators such as rituximab, and IL6 inhibitors such as tocilizumab.

The term "flare" as used herein is a sudden and severe increase in the onset of symptoms and clinical manifestations including, but not limited to, an increase in SJC, increase in TJC, increase in serologic markers of inflammation (e.g., CRP and ESR), decrease in subject function (e.g., ability to perform basic daily activities), increase in morning stiffness, and increases in pain that commonly lead to therapeutic intervention and potentially to treatment intensification.

An "immunoassay" as used herein refers to a biochemical assay that uses one or more antibodies to measure the presence or concentration of an analyte or biomarker in a biological sample.

"Inflammatory disease" in the context of the present teachings encompasses, without limitation, any disease, as defined herein, resulting from the biological response of vascular tissues to harmful stimuli, including but not limited to such stimuli as pathogens, damaged cells, irritants, antigens and, in the case of autoimmune disease, substances and tissues normally present in the body. Non-limiting examples of inflammatory disease include rheumatoid arthritis (RA), eRA, ankylosing spondylitis, psoriatic arthritis, atherosclerosis, asthma, autoimmune diseases, chronic inflammation, chronic prostatitis, glomerulonephritis, hypersensitivities, inflammatory bowel diseases, pelvic inflammatory disease, reperfusion injury, transplant rejection, and vasculitis.

"Interpretation function," as used herein, means the transformation of a set of observed data into a meaningful determination of particular interest; e.g., an interpretation function may be a predictive model that is created by utilizing one or more statistical algorithms to transform a dataset of observed biomarker data into a meaningful determination of disease activity or the disease state of a subject.

"Measuring" or "measurement" in the context of the present teachings refers to determining the presence, absence, quantity, amount, or effective amount of a substance in a clinical or subject-derived sample, including the concentration levels of such substances, or evaluating the values or categorization of a subject's clinical parameters.

A "multiplex assay" as used herein refers to an assay that simultaneously measure multiple analytes, e.g., protein analytes, in a single run or cycle of the assay.

"Performance" in the context of the present teachings relates to the quality and overall usefulness of, e.g., a model, algorithm, or diagnostic or prognostic test. Factors to be considered in model or test performance include, but are not limited to, the clinical and analytical accuracy of the test, use characteristics such as stability of reagents and various components, ease of use of the model or test, health or economic value, and relative costs of various reagents and components of the test. Performing can mean the act of carrying out a function.

A "population" is any grouping of subjects of like specified characteristics. The grouping could be according to, for example but without limitation, clinical parameters, clinical assessments, therapeutic regimen, disease status (e.g. with disease or healthy), level of disease activity, etc. In the context of using the BDAS score in comparing disease activity between populations, an aggregate value can be determined based on the observed BDAS scores of the subjects of a population; e.g., at particular timepoints in a longitudinal study. The aggregate value can be based on, e.g., any mathematical or statistical formula useful and known in the art for arriving at a meaningful aggregate value from a collection of individual datapoints; e.g., mean, median, median of the mean, etc.

A "predictive model," which term may be used synonymously herein with "multivariate model" or simply a "model," is a mathematical construct developed using a statistical algorithm or algorithms for classifying sets of data. The term "predicting" refers to generating a value for a datapoint without actually performing the clinical diagnostic procedures normally or otherwise required to produce that datapoint; "predicting" as used in this modeling context should not be understood solely to refer to the power of a model to predict a particular outcome. Predictive models can provide an interpretation function; e.g., a predictive model can be created by utilizing one or more statistical algorithms or methods to transform a dataset of observed data into a meaningful determination of disease activity or the disease state of a subject. See Calculation of the BDAS score for some examples of statistical tools useful in model development.

A "prognosis" is a prediction as to the likely outcome of a disease. Prognostic estimates are useful in, e.g., determining an appropriate therapeutic regimen for a subject.

A "quantitative dataset" or "quantitative data" as used in the present teachings, refers to the data derived from, e.g., detection and composite measurements of expression of a plurality of biomarkers (i.e., two or more) in a subject sample. The quantitative dataset can be used to generate a score for the identification, monitoring and treatment of disease states, and in characterizing the biological condition of a subject. It is possible that different biomarkers will be detected depending on the disease state or physiological condition of interest.

"Recommending" as used herein refers to making a recommendation for a therapeutic regimen or excluding (i.e., not recommending) a certain therapeutic regimen for a subject. Such a recommendation shall serve optionally together with other information as a basis for a clinician to apply a certain therapeutic regimen for an individual subject.

The term "remission" refers to the state of absence of disease activity in patients known to have a chronic illness that usually cannot be cured. The term "sustained clinical remission" or "SC-REM" as used herein refers to a state of clinical remission sustained as evaluated based on clinical assessments, for example, DAS28 for at least six months. The term "functional remission" as used herein refers to a state of remission as evaluated using functional assessment measures such as but not limited to HAQ. Sustained remission can be used interchangeably with maintained remission.

A "sample" in the context of the present teachings refers to any biological sample that is isolated from a subject. A sample can include, without limitation, a single cell or multiple cells, fragments of cells, an aliquot of body fluid, whole blood, platelets, serum, plasma, red blood cells, white blood cells or leucocytes, endothelial cells, tissue biopsies, synovial fluid, lymphatic fluid, ascites fluid, and interstitial or extracellular fluid. The term "sample" also encompasses the fluid in spaces between cells, including synovial fluid, gingival crevicular fluid, bone marrow, cerebrospinal fluid (CSF), saliva, mucous, sputum, semen, sweat, urine, or any other bodily fluids. "Blood sample" can refer to whole blood or any fraction thereof, including blood cells, red blood cells, white blood cells or leucocytes, platelets, serum and plasma. Samples can be obtained from a subject by means including but not limited to venipuncture, excretion, ejaculation, massage, biopsy, needle aspirate, lavage, scraping, surgical incision, or intervention or other means known in the art.

A "score" is a value or set of values selected so as to provide a quantitative measure of a variable or characteristic of a subject's condition, and/or to discriminate, differentiate or otherwise characterize a subject's condition. The value(s) comprising the score can be based on, for example, quantitative data resulting in a measured amount of one or more sample constituents obtained from the subject, or from clinical parameters, or from clinical assessments, or any combination thereof. In certain embodiments the score can be derived from a single constituent, parameter or assessment, while in other embodiments the score is derived from multiple constituents, parameters and/or assessments. The score can be based upon or derived from an interpretation function; e.g., an interpretation function derived from a particular predictive model using any of various statistical algorithms known in the art. A "change in score" can refer to the absolute change in score, e.g. from one time point to the next, or the percent change in score, or the change in the score per unit time (e.g., the rate of score change).

A "multiplex assay" as used herein refers to an assay that simultaneously measures multiple analytes, e.g., protein analytes, in a single run or cycle of the assay.

"Statistically significant" in the context of the present teachings means an observed alteration is greater than what would be expected to occur by chance alone (e.g., a "false positive"). Statistical significance can be determined by any of various methods well-known in the art. An example of a commonly used measure of statistical significance is the p-value. The p-value represents the probability of obtaining a given result equivalent to a particular datapoint, where the datapoint is the result of random chance alone. A result is often considered highly significant (not random chance) at a p-value less than or equal to 0.05.

A "subject" in the context of the present teachings is generally a mammal. The subject can be a patient. The term "mammal" as used herein includes but is not limited to a human, non-human primate, dog, cat, mouse, rat, cow, horse, and pig. Mammals other than humans can be advantageously used as subjects that represent animal models of inflammation. A subject can be male or female. A subject can be one who has been previously diagnosed or identified as having an inflammatory disease. A subject can be one who has already undergone, or is undergoing, a therapeutic intervention for an inflammatory disease. A subject can also be one who has not been previously diagnosed as having an inflammatory disease; e.g., a subject can be one who exhibits one or more symptoms or risk factors for an inflammatory condition, or a subject who does not exhibit symptoms or risk factors for an inflammatory condition, or a subject who is asymptomatic for inflammatory disease.

A "therapeutic regimen," "therapy" or "treatment(s)," as described herein, includes all clinical management of a subject and interventions, whether biological, chemical, physical, or a combination thereof, intended to sustain, ameliorate, improve, or otherwise alter the condition of a subject. These terms may be used synonymously herein. Treatments include but are not limited to administration of prophylactics or therapeutic compounds (including conventional DMARDs, biologic DMARDs, non-steroidal anti-inflammatory drugs (NSAID's) such as COX-2 selective inhibitors, and corticosteroids), exercise regimens, physical therapy, dietary modification and/or supplementation, bariatric surgical intervention, administration of pharmaceuticals and/or anti-inflammatories (prescription or over-the-counter), and any other treatments known in the art as efficacious in preventing, delaying the onset of, or ameliorating disease. A "response to treatment" includes a subject's response to any of the above-described treatments, whether biological, chemical, physical, or a combination of the foregoing. A "treatment course" relates to the dosage, duration, extent, etc. of a particular treatment or therapeutic regimen. An initial therapeutic regimen as used herein is the first line of treatment.

A "time point" as used herein refers to a manner of describing a time, which can be substantially described with a single point. A time point may also be described as a time range of a minimal unit which can be detected. A time point can refer to a state of the aspect of a time or a manner of description of a certain period of time. Such a time point or range can include, for example, an order of seconds, minutes to hours, or days.

Use of the Present Teachings in the Diagnosis, Prognosis, and Assessment of Disease In some embodiments of the present teachings, biomarkers can be used in the derivation of a BDAS score, as described herein, which BDAS score can be used to provide diagnosis, prognosis and monitoring of disease state and/or disease activity in inflammatory disease and in autoimmune disease. In certain embodiments, the BDAS score can be used to provide diagnosis, prognosis and monitoring of disease state and/or disease activity of RA or early RA in response to therapy. In certain embodiments, the BDAS score can be used to recommend discontinuation of a therapeutic regimen, or the BDAS score can be used to recommend no change in a therapeutic regimen.

Biomarkers useful for deriving a BDAS score can include Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotransferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B, Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1).

In some embodiments, biomarkers useful for deriving a BDAS score are selected from CPSD, SAP, PEDF, C-Peptide, tPA, TIG2, or FAS.

In some embodiments, biomarkers useful for deriving a BDAS score are selected from CPSD, A1M, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15.

In some embodiments, biomarkers useful for deriving a BDAS score are selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15.

In some embodiments, biomarkers useful for deriving a BDAS score are selected from CPSD, SAP, PEDF, C-peptide, tPA, TIG2, or FAS.

Identifying the state of inflammatory disease in a subject allows for a prognosis of the disease, and thus for the informed selection of, initiation of, adjustment of or increasing or decreasing various therapeutic regimens in order to delay, reduce or prevent that subject's progression to a more advanced disease state. In some embodiments, therefore, subjects can be identified as having a particular level of inflammatory disease activity and/or as being at a particular state of disease, or flare, based on the determination of their BDAS scores, and so can be selected to begin or accelerate treatment, as treatment is defined herein, to prevent or delay the further progression of inflammatory disease. In other embodiments, subjects that are identified via their BDAS scores as having a particular level of inflammatory disease activity, and/or as being at a particular state of inflammatory disease, can be selected to have their treatment decreased or discontinued, where improvement or remission in the subject is seen. In other embodiments, subjects that are identified via their BDAS scores as having a particular level of inflammatory disease activity, and/or as being at a particular state of inflammatory disease, can have therapy selected based on disease activity levels.

In regards to the need for early and accurate diagnosis of RA, recent advances in RA treatment provide a means for more profound disease management and optimal treatment of RA within the first months of symptom onset, which in turn result in significantly improved outcomes. See F. Wolfe, *Arth. Rheum.* 2000, 43(12):2751-2761; M. Matucci-Cerinic, *Clin. Exp. Rheum.* 2002, 20(4):443-444; and, V. Nell et. al., *Lancet* 2005, 365(9455):199-200. Unfortunately, most subjects do not receive optimal treatment within this narrow window of opportunity, resulting in poorer outcomes and irreversible joint damage, in part because of the limits of current diagnostic laboratory tests. Numerous difficulties exist in diagnosing RA subject. This is in part because at their early stages, symptoms may not be fully differentiated. It is also because diagnostic tests for RA were developed based on phenomenological findings, not the biological basis of disease. In various embodiments of the present teachings, multi-biomarker algorithms can be derived from the disclosed set of biomarkers.

Rating Disease Activity

In some embodiments of the present teachings, the BDAS score, derived as described herein, can be used to rate inflammatory disease activity; e.g., as high, medium or low. The score can be varied based on a set of values chosen by the practitioner. For example, a score can be set such that a value is given a range from 0-100, and a difference between two scores would be a value of at least one point. The practitioner can then assign disease activity based on the values. For example, in some embodiments a score of about 1 to 29 represents a low level of disease activity, a score of about 30 to 44 represents a moderate level of disease activity, and a score of about 45 to 100 represents a high level of disease activity. In some embodiments on a scale of 1-100 a score of ≤38 can represent a low or lower score, and a score of >38 can represent a high or higher score. In some embodiments on a scale of 1-100 a score of ≤30 can represent a low or lower score, and a score of >30 can represent a high or higher score. In some embodiments, an BDS scores of about ≤25 is remission, about 26-29 is low, about 30-44 is moderate, and about >44 is high. The cutoffs can vary. For example, in some embodiments a low score can be a score of <30, although for other utilities, a low score can be a score of <29 or <31.

The disease activity score can also change based on the range of the score. For example a score of 1 to 58 can represent a low level of disease activity when a range of 0-200 is utilized. Differences can be determined based on the range of score possibilities. For example, if using a score range of 0-100, a small difference in scores can be a difference of about 1, 2, 3, 4, 5, 6, 7, 8, 9, or 10 points; a moderate difference in scores can be a difference of about 4, 5, 6, 7, 8, 9, 10, 11, 12, 13, 14, 15, 16, 17, 18, 19, 20, 21, 22, 23, 24, 25, 26, 27, 28, 29, or 30 points; and large differences can be a change in about 14, 15, 16, 17, 18, 19, 20, 21, 22, 23, 24, 25, 26, 27, 28, 29, 30, 35, 40, 45, or 50 points. Thus, by way of example, a practitioner can define a small difference in scores as about ≤6 points, a moderate difference in scores as about 7-20 points, and a large difference in scores as about >20 points. The difference can be expressed by any unit, for example, percentage points. For example, a practitioner can define a small difference as about ≤6 percentage points, moderate difference as about 7-20 percentage points, and a large difference as about >20 percentage points.

In some embodiments of the present teachings, autoimmune disease activity can be so rated. In other embodiments, RA disease activity can be so rated. Because the BDAS score correlates well with traditional clinical assessments of inflammatory disease activity, e.g. in RA, in other embodiments of the present teachings bone damage itself in a subject or population, and thus disease progression, can be tracked via the use and application of the BDAS score.

The BDAS score can be used for several purposes. On a subject-specific basis, it provides a context for understanding the relative level of disease activity. The BDAS rating of disease activity can be used, e.g., to guide the clinician in determining treatment, in setting a treatment course, and/or to inform the clinician that the subject is in remission. Moreover, it provides a means to more accurately assess and document the qualitative level of disease activity in a subject. It is also useful from the perspective of assessing clinical differences among populations of subjects within a practice. For example, this tool can be used to assess the relative efficacy of different treatment modalities. Moreover, it is also useful from the perspective of assessing clinical differences among different practices. This would allow physicians to determine what global level of disease control is achieved by their colleagues, and/or for healthcare management groups to compare their results among different practices for both cost and comparative effectiveness. Because the BDAS score demonstrates strong association with established disease activity assessments, such as the DAS28, the BDAS score can provide a quantitative measure for monitoring the extent of subject disease activity, and response to treatment.

Subject Screening

Certain embodiments of the present teachings can also be used to screen subject populations in any number of settings. For example, a health maintenance organization, public health entity or school health program can screen a group of subjects to identify those requiring interventions, as described above. Other embodiments of these teachings can be used to collect disease activity data on one or more populations of subjects, to identify subject disease status in the aggregate, in order to, e.g., determine the effectiveness of the clinical management of a population, or determine gaps in clinical management. Insurance companies (e.g., health, life, or disability) may request the screening of applicants in the process of determining coverage for possible intervention. Data collected in such population screens, particularly when tied to any clinical progression to conditions such as inflammatory disease and RA, will be of value in the operations of, for example, health maintenance organizations, public health programs and insurance companies.

Such data arrays or collections can be stored in machine-readable media and used in any number of health-related data management systems to provide improved healthcare services, cost-effective healthcare, and improved insurance operation, among other things. See, e.g., U.S. Patent Application No. 2002/0038227; U.S. Patent Application No. 2004/0122296; U.S. Patent Application No. 2004/0122297; and U.S. Pat. No. 5,018,067. Such systems can access the data directly from internal data storage or remotely from one or more data storage sites as further detailed herein. Thus, in a health-related data management system, wherein it is important to manage inflammatory disease progression for a population in order to reduce disease-related employment productivity loss, disability and surgery, and thus reduce healthcare costs in the aggregate, various embodiments of the present teachings provide an improvement comprising the use of a data array encompassing the biomarker measurements as defined herein, and/or the resulting evaluation of disease status and activity from those biomarker measurements.

Calculation of Scores

In some embodiments of the present teachings, inflammatory disease activity in a subject is measured by: determining the levels in inflammatory disease subject serum of two or more biomarkers, then applying an interpretation function to transform the biomarker levels into a single BDAS score, which provides a quantitative measure of inflammatory disease activity in the subject, correlating well with traditional clinical assessments of inflammatory disease activity (e.g., a DAS28 or CDAI score in RA), as is demonstrated in the Examples below. In some embodiments, the disease activity so measured relates to an autoimmune disease. In some embodiments, the disease activity so measured relates to RA. The biomarkers can include Serum Amyloid P-component (SAP), Cathepsin D (CPSD), Chemerin (TIG2), alpha-1-Microglobulin (A1M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation-Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), von Willebrand Factor (vWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotransferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Antileukoproteinase (ALP), Thymus and activation-regulated chemokine (TARC), Plasminogen Activator Inhibitor 1 (PAI-1), Interleukin-15 (IL-15), Ceruloplasmin (CP), Complement Factor H—Related Protein 1 (CFHR1), Protein DJ-1 (DJ-1), Alpha-Fetoprotein (AFP), Chemokine CC-4 (HCC-4), Ferritin (FRTN), Interleukin-15 (IL-15), Immunoglobulin A (IgA), thrombin-Activatable Fibrinolysis (TAFI), Cystatin-B, Alpha-1-Antichymotrypsin (AACT) Pancreatic Polypeptide (PPP), Heat-Shock Protein 70 (HSP-70), Transferrin Receptor Protein (TFR1), Tamm-Horsfall Urinary Glycoprotein (THP) Tenascin-C (TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (IGFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), or Monocyte Chemotactic Protein 1 (MCP-1).

In some embodiments, biomarkers useful for deriving a BDAS score are selected from CPSD, SAP, PEDF, C-Peptide, tPA, TIG2, or FAS.

In some embodiments, biomarkers useful for deriving a BDAS score are selected from CPSD, A1M, TIG2, C-Peptide, tPA, SHBG, GDF-15, Hp, CD5L, AGP-1, CLU, FAS, CRP, CFH, RAGE, FGF-21, vWF, CRP, AACT, CSTB, ST2, TAFI, uPA, TN, Prx-IV, Tweak, PSAT, GLP-1 total, or IL-15.

In some embodiments, biomarkers useful for deriving a BDAS score are selected from CPSD, PEDF, SAP, SHBG, A1M, tPA, AGP-1, TIG2, CD5L, FAS, C-Peptide, CRP, PSAT, uPA, GIP, Prx-IV, HGF, or IL-15.

In some embodiments, biomarkers useful for deriving a BDAS score are selected from CPSD, SAP, PEDF, C-peptide, tPA, TIG2, or FAS.

In some embodiments, the interpretation function is based on a predictive model. Established statistical algorithms and methods well-known in the art, useful as models or useful in designing predictive models, can include but are not limited to: analysis of variants (ANOVA); Bayesian networks; boosting and Ada-boosting; bootstrap aggregating (or bagging) algorithms; decision trees classification techniques, such as Classification and Regression Trees (CART), boosted CART, Random Forest (RF), Recursive Partitioning Trees (RPART), and others; Curds and Whey (CW); Curds and Whey-Lasso; dimension reduction methods, such as principal component analysis (PCA) and factor rotation or factor analysis; discriminant analysis, including Linear Discriminant Analysis (LDA), Eigengene Linear Discriminant Analysis (ELDA), and quadratic discriminant analysis; Discriminant Function Analysis (DFA); factor rotation or factor analysis; genetic algorithms; Hidden Markov Models; kernel based machine algorithms such as kernel density estimation, kernel partial least squares algorithms, kernel matching pursuit algorithms, kernel Fisher's discriminate analysis algorithms, and kernel principal components analysis algorithms; linear regression and generalized linear models, including or utilizing Forward Linear Stepwise Regression, Lasso (or LASSO) shrinkage and selection method, and Elastic Net regularization and selection method; glmnet (Lasso and Elastic Net-regularized generalized linear model); Logistic Regression (LogReg); meta-learner algorithms; nearest neighbor methods for classification or regression, e.g. Kth-nearest neighbor (KNN); non-linear regression or classification algorithms; neural networks; partial least square; rules based classifiers; shrunken centroids (SC); sliced inverse regression; Standard for the Exchange of Product model data, Application Interpreted Constructs (StepAIC); super principal component (SPC) regression; and, Support Vector Machines (SVM) and Recursive Support Vector Machines (RSVM), among others. Additionally, clustering algorithms as are known in the art can be useful in determining subject sub-groups.

Logistic Regression is the traditional predictive modeling method of choice for dichotomous response variables; e.g., treatment 1 versus treatment 2. It can be used to model both linear and non-linear aspects of the data variables and provides easily interpretable odds ratios.

Discriminant Function Analysis (DFA) uses a set of analytes as variables (roots) to discriminate between two or more naturally occurring groups. DFA is used to test analytes that are significantly different between groups. A forward step-wise DFA can be used to select a set of analytes that maximally discriminate among the groups studied. Specifically, at each step all variables can be reviewed to determine which will maximally discriminate among groups. This information is then included in a discriminative function, denoted a root, which is an equation consisting of linear combinations of analyte concentrations for the prediction of group membership. The discriminatory potential of the final equation can be observed as a line plot of the root values obtained for each group. This approach identifies groups of analytes whose changes in concentration levels can be used to delineate profiles, diagnose and assess therapeutic efficacy. The DFA model can also create an arbitrary score by which new subjects can be classified as either "healthy" or "diseased." To facilitate the use of this score for the medical community the score can be rescaled so a value of 0 indicates a healthy individual and scores greater than 0 indicate increasing disease activity.

Classification and regression trees (CART) perform logical splits (if/then) of data to create a decision tree. All observations that fall in a given node are classified according to the most common outcome in that node. CART results are easily interpretable—one follows a series of if/then tree branches until a classification results.

Support vector machines (SVM) classify objects into two or more classes. Examples of classes include sets of treatment alternatives, sets of diagnostic alternatives, or sets of prognostic alternatives. Each object is assigned to a class based on its similarity to (or distance from) objects in the training data set in which the correct class assignment of each object is known. The measure of similarity of a new object to the known objects is determined using support vectors, which define a region in a potentially high dimensional space (>R6).

The process of bootstrap aggregating, or "bagging," is computationally simple. In the first step, a given dataset is randomly resampled a specified number of times (e.g., thousands), effectively providing that number of new datasets, which are referred to as "bootstrapped resamples" of data, each of which can then be used to build a model. Then, in the example of classification models, the class of every new observation is predicted by the number of classification models created in the first step. The final class decision is based upon a "majority vote" of the classification models; i.e., a final classification call is determined by counting the number of times a new observation is classified into a given group, and taking the majority classification (33%+ for a three-class system). In the example of logistical regression models, if a logistical regression is bagged 1000 times, there will be 1000 logistical models, and each will provide the probability of a sample belonging to class 1 or 2.

Curds and Whey (CW) using ordinary least squares (OLS) is another predictive modeling method. See L. Breiman and J H Friedman, *J. Royal. Stat. Soc. B* 1997, 59(1):3-54. This method takes advantage of the correlations between response variables to improve predictive accuracy, compared with the usual procedure of performing an individual regression of each response variable on the common set of predictor variables X. In CW, Y=XB*S, where Y=($y_{kj}$) with k for the $k^{th}$ patient and j for $j^{th}$ response (j=1 for TJC, j=2 for SJC, etc.), B is obtained using OLS, and S is the shrinkage matrix computed from the canonical coordinate system. Another method is Curds and Whey and Lasso in combination (CW-Lasso). Instead of using OLS to obtain B, as in CW, here Lasso is used, and parameters are adjusted accordingly for the Lasso approach.

Many of these techniques are useful either combined with a biomarker selection technique (such as, for example, forward selection, backwards selection, or stepwise selection), or for complete enumeration of all potential panels of a given size, or genetic algorithms, or they can themselves include biomarker selection methodologies in their own techniques. These techniques can be coupled with information criteria, such as Akaike's Information Criterion (AIC), Bayes Information Criterion (BIC), or cross-validation, to quantify the tradeoff between the inclusion of additional biomarkers and model improvement, and to minimize overfit. The resulting predictive models can be validated in other studies, or cross-validated in the study they were originally trained in, using such techniques as, for example, Leave-One-Out (LOO) and 10-Fold cross-validation (10-Fold CV).

One example of an interpretation function that provides a BDAS score, derived from a statistical modeling method as described above, is given by the following function:

$$BDAS=(BM1conc*(0.39^{\wedge}0.5)+BM2conc*(0.39^{\wedge}0.5)+BM3conc*(0.39^{\wedge}0.5)+BM4conc*(0.36^{\wedge}0.5)+BM5conc*(0.31^{\wedge}0.5))/10$$

BDAS scores thus obtained for RA subjects with known clinical assessments (e.g., DAS28 scores) can then be compared to those known assessments to determine the level of correlation between the two assessments, and hence determine the accuracy of the BDAS score and its underlying predictive model. See Examples below for specific formulas and constants.

In some embodiments of the present teachings, it is not required that the BDAS score be compared to any predetermined "reference," "normal," "control," "standard," "healthy," "pre-disease" or other like index, in order for the BDAS score to provide a quantitative measure of inflammatory disease activity in the subject.

In other embodiments of the present teachings, the amount of the biomarker(s) can be measured in a sample and used to derive a BDAS score, which BDAS score is then compared to a "normal" or "control" level or value, utilizing techniques such as, e.g., reference or discrimination limits or risk defining thresholds, in order to define cut-off points and/or abnormal values for inflammatory disease. The normal level then is the level of one or more biomarkers or combined biomarker indices typically found in a subject who is not suffering from the inflammatory disease under evaluation. Other terms for "normal" or "control" are, e.g., "reference," "index," "baseline," "standard," "healthy," "pre-disease," etc. Such normal levels can vary, based on whether a biomarker is used alone or in a formula combined with other biomarkers to output a score. Alternatively, the normal level can be a database of biomarker patterns from previously tested subjects who did not convert to the inflammatory disease under evaluation over a clinically relevant time period. Reference (normal, control) values can also be derived from, e.g., a control subject or population whose inflammatory disease activity level or state is known. In some embodiments of the present teachings, the reference value can be derived from one or more subjects who have been exposed to treatment for inflammatory disease, or from one or more subjects who are at low risk of developing inflammatory disease, or from subjects who have shown improvements in inflammatory disease activity factors (such as, e.g., clinical parameters as defined herein) as a result of exposure to treatment. In some embodiments the reference value can be derived from one or more subjects who have not been exposed to treatment; for example, samples can be collected from (a) subjects who have received initial treatment for inflammatory disease, and (b) subjects who have received subsequent treatment for inflammatory disease, to monitor the progress of the treatment. A reference value can also be derived from disease activity algorithms or computed indices from population studies.

Measurement of Biomarkers

The quantity of one or more biomarkers of the present teachings can be indicated as a value. The value can be one or more numerical values resulting from the evaluation of a sample, and can be derived, e.g., by measuring level(s) of the biomarker(s) in a sample by an assay performed in a laboratory, or from dataset obtained from a provider such as a laboratory, or from a dataset stored on a server. Biomarker levels can be measured using any of several techniques known in the art. The present teachings encompass such techniques, and further include all subject fasting and/or temporal-based sampling procedures for measuring biomarkers.

The actual measurement of levels of the biomarkers can be determined at the protein or nucleic acid level using any method known in the art. "Protein" detection comprises detection of full-length proteins, mature proteins, pre-proteins, polypeptides, isoforms, mutations, variants, post-translationally modified proteins and variants thereof, and can be detected in any suitable manner. Levels of biomarkers can be determined at the protein level, e.g., by measuring the serum levels of peptides encoded by the gene products described herein, or by measuring the enzymatic activities of these protein biomarkers. Such methods are well-known in the art and include, e.g., immunoassays based on antibodies to proteins encoded by the genes, aptamers or molecular imprints. Any biological material can be used for the detection/quantification of the protein or its activity. Alternatively, a suitable method can be selected to determine the activity of proteins encoded by the biomarker genes according to the activity of each protein analyzed. For biomarker proteins, polypeptides, isoforms, mutations, and variants thereof known to have enzymatic activity, the activities can be determined in vitro using enzyme assays known in the art. Such assays include, without limitation, protease assays, kinase assays, phosphatase assays, reductase assays, among many others. Modulation of the kinetics of enzyme activities can be determined by measuring the rate constant KM using known algorithms, such as the Hill plot, Michaelis-Menten equation, linear regression plots such as Lineweaver-Burk analysis, and Scatchard plot.

Using sequence information provided by the public database entries for the biomarker, expression of the biomarker can be detected and measured using techniques well-known to those of skill in the art. For example, nucleic acid sequences in the sequence databases that correspond to nucleic acids of biomarkers can be used to construct primers and probes for detecting and/or measuring biomarker nucleic acids. These probes can be used in, e.g., Northern or Southern blot hybridization analyses, ribonuclease protection assays, and/or methods that quantitatively amplify specific nucleic acid sequences. As another example, sequences from sequence databases can be used to construct primers for specifically amplifying biomarker sequences in, e.g., amplification-based detection and quantitation methods such as reverse-transcription based polymerase chain reaction (RT-PCR) and PCR. When alterations in gene expression are associated with gene amplification, nucleotide deletions, polymorphisms, post-translational modifications and/or mutations, sequence comparisons in test and reference populations can be made by comparing relative amounts of the examined DNA sequences in the test and reference populations.

As an example, Northern hybridization analysis using probes which specifically recognize one or more of these sequences can be used to determine gene expression. Alternatively, expression can be measured using RT-PCR; e.g., polynucleotide primers specific for the differentially expressed biomarker mRNA sequences reverse-transcribe the mRNA into DNA, which is then amplified in PCR and can be visualized and quantified. Biomarker RNA can also be quantified using, for example, other target amplification methods, such as TMA, SDA, and NASBA, or signal amplification methods (e.g., bDNA), and the like. Ribonuclease protection assays can also be used, using probes that specifically recognize one or more biomarker mRNA sequences, to determine gene expression.

Alternatively, biomarker protein and nucleic acid metabolites can be measured. The term "metabolite" includes any chemical or biochemical product of a metabolic process, such as any compound produced by the processing, cleavage or consumption of a biological molecule (e.g., a protein, nucleic acid, carbohydrate, or lipid). Metabolites can be detected in a variety of ways known to one of skill in the art, including the refractive index spectroscopy (RI), ultra-violet spectroscopy (UV), fluorescence analysis, radiochemical analysis, near-infrared spectroscopy (near-IR), nuclear magnetic resonance spectroscopy (NMR), light scattering analysis (LS), mass spectrometry, pyrolysis mass spectrometry, nephelometry, dispersive Raman spectroscopy, gas chromatography combined with mass spectrometry, liquid chromatography combined with mass spectrometry, matrix-assisted laser desorption ionization-time of flight (MALDI-TOF) combined with mass spectrometry, ion spray spectroscopy combined with mass spectrometry, capillary electrophoresis, NMR and IR detection. See WO 04/056456 and WO 04/088309, each of which is hereby incorporated by reference in its entirety. In this regard, other biomarker analytes can be measured using the above-mentioned detection methods, or other methods known to the skilled artisan. For example, circulating calcium ions ($Ca^{2+}$) can be detected in a sample using fluorescent dyes such as the Fluo series, Fura-2A, Rhod-2, among others. Other biomarker metabolites can be similarly detected using reagents that are specifically designed or tailored to detect such metabolites.

In some embodiments, a biomarker is detected by contacting a subject sample with reagents, generating complexes of reagent and analyte, and detecting the complexes. Examples of "reagents" include but are not limited to nucleic acid primers and antibodies.

In some embodiments of the present teachings an antibody binding assay is used to detect a biomarker; e.g., a sample from the subject is contacted with an antibody reagent that binds the biomarker analyte, a reaction product (or complex) comprising the antibody reagent and analyte is generated, and the presence (or absence) or amount of the complex is determined. The antibody reagent useful in detecting biomarker analytes can be monoclonal, polyclonal, chimeric, recombinant, or a fragment of the foregoing, as discussed in detail above, and the step of detecting the reaction product can be carried out with any suitable immunoassay. The sample from the subject is typically a biological fluid as described above, and can be the same sample of biological fluid as is used to conduct the method described above.

Immunoassays carried out in accordance with the present teachings can be homogeneous assays or heterogeneous assays. Immunoassays carried out in accordance with the present teachings can be multiplexed. In a homogeneous assay the immunological reaction can involve the specific antibody (e.g., anti-biomarker protein antibody), a labeled analyte, and the sample of interest. The label produces a signal, and the signal arising from the label becomes modified, directly or indirectly, upon binding of the labeled analyte to the antibody. Both the immunological reaction of binding, and detection of the extent of binding, can be carried out in a homogeneous solution. Immunochemical labels which can be employed include but are not limited to free radicals, radioisotopes, fluorescent dyes, enzymes, bacteriophages, and coenzymes. Immunoassays include competition assays.

In a heterogeneous assay approach, the reagents can be the sample of interest, an antibody, and a reagent for producing a detectable signal. Samples as described above can be used. The antibody can be immobilized on a support, such as a bead (such as protein A and protein G agarose beads), plate or slide, and contacted with the sample suspected of containing the biomarker in liquid phase. The support is separated from the liquid phase, and either the support phase or the liquid phase is examined using methods known in the art for detecting signal. The signal is related to the presence of the analyte in the sample. Methods for producing a detectable signal include but are not limited to the use of radioactive labels, fluorescent labels, or enzyme labels. For example, if the antigen to be detected contains a second binding site, an antibody which binds to that site can be conjugated to a detectable (signal-generating) group and added to the liquid phase reaction solution before the separation step. The presence of the detectable group on the solid support indicates the presence of the biomarker in the test sample. Examples of suitable immunoassays include but are not limited to oligonucleotides, immunoblotting, immunoprecipitation, immunofluorescence methods, chemiluminescence methods, electrochemiluminescence (ECL), and/or enzyme-linked immunoassays (ELISA).

Those skilled in the art will be familiar with numerous specific immunoassay formats and variations thereof which can be useful for carrying out the method disclosed herein. See, e.g., E. Maggio, *Enzyme-Immunoassay* (1980), CRC Press, Inc., Boca Raton, Fla. See also U.S. Pat. No. 4,727,022 to C. Skold et al., titled "Novel Methods for Modulating Ligand-Receptor Interactions and their Application"; U.S. Pat. No. 4,659,678 to GC Forrest et al., titled "Immunoassay of Antigens"; U.S. Pat. No. 4,376,110 to GS David et al., titled "Immunometric Assays Using Monoclonal Antibodies"; U.S. Pat. No. 4,275,149 to D. Litman et al., titled "Macromolecular Environment Control in Specific Receptor Assays"; U.S. Pat. No. 4,233,402 to E. Maggio et al., titled "Reagents and Method Employing Channeling"; and, U.S. Pat. No. 4,230,797 to R. Boguslaski et al., titled "Heterogenous Specific Binding Assay Employing a Coenzyme as Label."

Antibodies can be conjugated to a solid support suitable for a diagnostic assay (e.g., beads such as protein A or protein G agarose, microspheres, plates, slides or wells formed from materials such as latex or polystyrene) in accordance with known techniques, such as passive binding. Antibodies as described herein can likewise be conjugated to detectable labels or groups such as radiolabels (e.g., 35S, 125I, 131I), enzyme labels (e.g., horseradish peroxidase, alkaline phosphatase), and fluorescent labels (e.g., fluorescein, Alexa, green fluorescent protein, rhodamine) in accordance with known techniques.

Antibodies may also be useful for detecting post-translational modifications of biomarkers. Examples of post-translational modifications include, but are not limited to tyrosine phosphorylation, threonine phosphorylation, serine phosphorylation, citrullination and glycosylation (e.g., O-GlcNAc). Such antibodies specifically detect the phosphorylated amino acids in a protein or proteins of interest, and can be used in the immunoblotting, immunofluorescence, and ELISA assays described herein. These antibodies are well-known to those skilled in the art, and commercially available. Post-translational modifications can also be determined using metastable ions in reflector matrix-assisted laser desorption ionization-time of flight mass spectrometry (MALDI-TOF). See U. Wirth et al., *Proteomics* 2002, 2(10): 1445-1451.

Therapeutic Regimens

The present invention provides methods of recommending therapeutic regimens, including withdrawal from therapeutic regimens, following the determination of differences in expression of the biomarkers disclosed herein. Measuring scores derived from expression levels of the biomarkers disclosed herein over a period time can provide a clinician with a dynamic picture of a subject's biological state. These embodiments of the present teachings thus will provide subject-specific biological information, which will be informative for therapy decision and will facilitate therapy response monitoring, and should result in more rapid and more optimized treatment, better control of disease activity, and an increase in the proportion of subjects achieving remission.

Treatment strategies for autoimmune disorders are confounded by the fact that some autoimmune disorders, such as RA, is a classification given to a group of subjects with a diverse array of related symptoms that can flare or go into remission. This suggests that certain subtypes of RA are driven by specific cell type or cytokine. As a likely consequence, no single therapy has proven optimal for treatment. Given the increasing numbers of therapeutic options available for RA, the need for an individually tailored treatment directed by immunological prognostic factors of treatment outcome is imperative. In various embodiments of the present teachings, a biomarker-derived algorithm can be used to quantify therapy response in RA subjects. For patients with early RA (eRA), methotrexate (MTX) is sometimes recommended as a first-line treatment and in non-responders both the addition of conventional non-biological disease modifying anti-rheumatic drug therapy (triple DMARD therapy) and of biological (anti-TNF) therapy are supported by data. Identification of patients with a higher likelihood of responding to one or the other of these options would lead to more personalized medicine and increased effectiveness of therapy, which is a primary objective of this invention.

In some embodiments, prediction of autoimmune disease patients, in particular RA patients, who can successfully withdrawal from or discontinue therapy, can be based on a BDAS score. In some embodiments, a high BDAS score as described herein at baseline can be an independent predictor of disease progression within a certain period of time following discontinuation of therapy. In some embodiments, a moderate BDAS score as described herein at baseline can be an independent predictor of disease progression within a certain period of time following discontinuation of therapy. In some embodiments, a low BDAS score as described herein at baseline can be an independent predictor of disease progression, or remission, within a certain period of time following discontinuation of therapy.

Reference Standards for Treatment

In many embodiments, the levels of one or more analyte biomarkers or the levels of a specific panel of analyte biomarkers in a sample are compared to a reference standard ("reference standard" or "reference level") in order to direct treatment decisions. Expression levels of the one or more biomarkers can be combined into a score, which can represent disease activity. The reference standard used for any embodiment disclosed herein may comprise average, mean, or median levels of the one or more analyte biomarkers or the levels of the specific panel of analyte biomarkers in a control population. The reference standard may further include an earlier time point for the same subject. For example, a reference standard may include a first time point, and the levels of the one or more analyte biomarkers can be examined again at second, third, fourth, fifth, sixth time points, etc. Any time point earlier than any particular time point can be considered a reference standard. The reference standard may additionally comprise cutoff values or any other statistical attribute of the control population, or earlier time points of the same subject, such as a standard deviation from the mean levels of the one or more analyte biomarkers or the levels of the specific panel of analyte biomarkers. In some embodiments, the control population may comprise healthy individuals or the same subject prior to the administration of any therapy.

In some embodiments, a score may be obtained from the reference time point, and a different score may be obtained from a later time point. A first time point can be when an initial therapeutic regimen is begun. A first time point can also be when a first immunoassay is performed. A time point can be hours, days, months, years, etc. In some embodiments, a time point is one month. In some embodiments, a time point is two months. In some embodiments, a time point is three months. In some embodiments, a time point is four months. In some embodiments, a time point is five months. In some embodiments, a time point is six months. In some embodiments, a time point is seven months. In some embodiments, a time point is eight months. In some embodiments, a time point is nine months. In some embodiments, a time point is ten months. In some embodiments, a time point is eleven months. In some embodiments, a time point is twelve months. In some embodiments, a time point is two years. In some embodiments, a time point is three years. In some embodiments, a time point is four years. In some embodiments, a time point is five years. In some embodiments, a time point is ten years.

A difference in the score can be interpreted as a decrease in disease activity. For example, lower score can indicate a lower level of disease activity, or remission. In these circumstances a second score having a lower score than the reference score, or first score, means that the subject's disease activity has been lowered (improved) between the first and second time periods, or is in remission. Alternatively, a higher score can indicate a lower level of disease activity, or remission. In these circumstances, a second score having a higher score than the reference score, or first score, also means that the subject's disease activity has improved between the first and second time periods, or is in remission.

A difference in the score can also be interpreted as an increase in disease activity. For example, lower score can indicate a higher level of disease activity, or flare. In these circumstances a second score having a lower score than the reference score, or first score, means that the subject's disease activity has been increased (worsened) between the first and second time periods. Alternatively, a higher score can indicate a higher level of disease activity, or flare. In these circumstances, a second score having a higher score than the reference score, or first score, also means that the subject's disease activity has worsened between the first and second time periods, or is flaring.

The differences can be variable. For example, when a difference in the score is interpreted as a decrease in disease activity, a large difference can mean a greater decrease in disease activity than a lower or moderate difference. Alternatively, when a difference in the score is interpreted as an increase in disease activity, a large difference can mean a greater increase in disease activity than a lower or moderate difference.

Reference Therapy for Treatment

In some embodiments, a patient is treated more or less aggressively than a reference therapy based on the difference of scores. A reference therapy is any therapy that is the standard of care for the autoimmune disorder. The standard of care can vary temporally and geographically, and a skilled person can easily determine the appropriate standard of care by consulting the relevant medical literature.

In some embodiments, a more aggressive therapy than the standard therapy comprises beginning treatment earlier than in the standard therapy. In some embodiments, a more aggressive therapy than the standard therapy comprises administering additional treatments than in the standard therapy. In some embodiments, a more aggressive therapy than the standard therapy comprises treating on an accelerated schedule compared to the standard therapy. In some embodiments, a more aggressive therapy than the standard therapy comprises administering additional treatments not called for in the standard therapy.

In some embodiments, a less aggressive therapy than the standard therapy comprises delaying treatment relative to the standard therapy. In some embodiments, a less aggressive therapy than the standard therapy comprises administering less treatment than in the standard therapy. In some embodiments, a less aggressive therapy than the standard therapy comprises administering treatment on a decelerated schedule compared to the standard therapy. In some embodiments, a less aggressive therapy than the standard therapy comprises administering no treatment.

Treatment of Autoimmune Disorders

In one embodiment, the practitioner discontinues a therapy regimen if a score is low. In one embodiment, the practitioner does not change the therapy regimen if the score is high. In one embodiment, the practitioner adjusts the therapy based on a comparison between difference scores, or based on an initial predictive score. In one embodiment, the practitioner adjusts the therapy by selecting and administering a different drug. In one embodiment, the practitioner adjusts the therapy by selecting and administering a different combination of drugs. In one embodiment, the practitioner adjusts the therapy by adjusting drug dosage. In one embodiment, the practitioner adjusts the therapy by adjusting dose schedule. In one embodiment, the practitioner adjusts the therapy by adjusting length of therapy. In one embodiment, the practitioner adjusts the therapy by selecting and administering a different drug combination and adjusting drug dosage. In one embodiment, the practitioner adjusts the therapy by selecting and administering a different drug combination and adjusting dose schedule. In one embodiment, the practitioner adjusts the therapy by selecting and administering a different drug combination and adjusting length of therapy. In one embodiment, the practitioner adjusts the therapy by adjusting drug dosage and dose schedule. In one embodiment, the practitioner adjusts the therapy by adjusting drug dosage and adjusting length of therapy. In one embodiment, the practitioner adjusts the therapy by adjusting dose schedule and adjusting length of therapy. In one embodiment, the practitioner adjusts the therapy by selecting and administering a different drug, adjusting drug dosage, and adjusting dose schedule. In one embodiment, the practitioner adjusts the therapy by selecting and administering a different drug, adjusting drug dosage, and adjusting length of therapy. In one embodiment, the practitioner adjusts the therapy by selecting and administering a different drug, adjusting dose schedule, and adjusting length of therapy. In one embodiment, the practitioner adjusts the therapy by adjusting drug dosage, adjusting dose schedule, and adjusting length of therapy. In one embodiment, the practitioner adjusts the therapy by selecting and administering a different drug, adjusting drug dosage, adjusting dose schedule, and adjusting length of therapy.

In one embodiment a less aggressive therapy comprises no change in the therapy regimen. In one embodiment a less aggressive therapy comprises delaying treatment. In one embodiment a less aggressive therapy comprises selecting and administering less potent drugs. In one embodiment a less aggressive therapy comprises decreasing the frequency treatment. In one embodiment a less aggressive therapy comprises shortening length of therapy. In one embodiment, less aggressive therapy comprises selecting and administering less potent drugs and decreasing drug dosage. In one embodiment, less aggressive therapy comprises selecting and administering less potent drugs and decelerating dose schedule. In one embodiment, less aggressive therapy comprises selecting and administering less potent drugs and shortening length of therapy. In one embodiment, less aggressive therapy comprises decreasing drug dosage and decelerating dose schedule. In one embodiment, less aggressive therapy comprises decreasing drug dosage and shortening length of therapy. In one embodiment, less aggressive therapy comprises decelerating dose schedule and shortening length of therapy. In one embodiment, less aggressive therapy comprises selecting and administering less potent drugs, decreasing drug dosage, and decelerating dose schedule. In one embodiment, less aggressive therapy comprises selecting and administering less potent drugs, decreasing drug dosage, and shortening length of therapy. In one embodiment, less aggressive therapy comprises selecting and administering less potent drugs, decelerating dose schedule, and shortening length of therapy. In one embodiment, less aggressive therapy comprises decreasing drug dosage, decelerating dose schedule, and shortening length of therapy. In one embodiment, less aggressive therapy comprises selecting and administering less potent drugs, decreasing drug dosage, decelerating dose schedule, and shortening length of therapy. In some embodiments, a less aggressive therapy comprises administering only non-drug-based therapies.

In another aspect of the present application, treatment comprises a more aggressive therapy than a reference therapy. In one embodiment a more aggressive therapy comprises increased length of therapy. In one embodiment a more aggressive therapy comprises increased frequency of the dose schedule. In one embodiment, more aggressive therapy comprises selecting and administering more potent drugs and increasing drug dosage. In one embodiment, more aggressive therapy comprises selecting and administering more potent drugs and accelerating dose schedule. In one embodiment, more aggressive therapy comprises selecting and administering more potent drugs and increasing length of therapy. In one embodiment, more aggressive therapy comprises increasing drug dosage and accelerating dose schedule. In one embodiment, more aggressive therapy comprises increasing drug dosage and increasing length of therapy. In one embodiment, more aggressive therapy comprises accelerating dose schedule and increasing length of therapy. In one embodiment, more aggressive therapy comprises selecting and administering more potent drugs, increasing drug dosage, and accelerating dose schedule. In one embodiment, more aggressive therapy comprises selecting and administering more potent drugs, increasing drug dosage, and increasing length of therapy. In one embodiment, more aggressive therapy comprises selecting and administering more potent drugs, accelerating dose schedule, and increasing length of therapy. In one embodiment, more aggressive therapy comprises increasing drug dosage, accelerating dose schedule, and increasing length of therapy. In one embodiment, more aggressive therapy comprises selecting and administering more potent drugs, increasing drug dosage, accelerating dose schedule, and increasing length of therapy. In some embodiments, a more aggressive therapy comprises administering a combination of drug-based therapies, non-drug-based therapies, or a combination of classes of drug-based therapies.

Therapies can be conventional or biologic. Examples of therapies, such as disease modifying anti-rheumatic drugs (DMARD) that are generally considered conventional include, but are not limited to, MTX, azathioprine (AZA), bucillamine (BUC), chloroquine (CQ), ciclosporin (CSA, or cyclosporine, or cyclosporin), doxycycline (DOXY), hydroxychloroquine (HCQ), intramuscular gold (IM gold), leflunomide (LEF), levofloxacin (LEV), and sulfasalazine (SSZ). Examples of other conventional therapies include, but are not limited to, folinic acid, D-pencillamine, gold auranofin, gold aurothioglucose, gold thiomalate, cyclophosphamide, and chlorambucil. Examples of biologic drugs can include but are not limited to biological agents that target the tumor necrosis factor (TNF)-alpha molecules and the TNF inhibitors, such as infliximab, adalimumab, etanercept and golimumab. Other classes of biologic drugs include IL1 inhibitors such as anakinra, T-cell modulators such as abatacept, B-cell modulators such as rituximab, and IL6 inhibitors such as tocilizumab.

To identify additional therapeutics or drugs that are appropriate for a specific subject, a test sample from the subject can also be exposed to a therapeutic agent or a drug, and the level of one or more biomarkers can be determined. The level of one or more biomarkers can be compared to sample derived from the subject before and after treatment or exposure to a therapeutic agent or a drug, or can be compared to samples derived from one or more subjects who have shown improvements in inflammatory disease state or activity (e.g., clinical parameters or traditional laboratory risk factors) as a result of such treatment or exposure.

Clinical Assessments of the Present Teachings

In some embodiments of the present teachings, BDAS scores are tailored to the population, endpoints or clinical assessment, and/or use that is intended. For example, a BDAS score can be used to assess subjects for primary prevention and diagnosis, and for secondary prevention and management. For the primary assessment, the BDAS score can be used for prediction and risk stratification for future conditions or disease sequelae, for the diagnosis of inflammatory disease, for the prognosis of disease activity and rate of change, and for indications for future diagnosis and therapeutic regimens. For secondary prevention and clinical management, the BDAS score can be used for prognosis and risk stratification. The BDAS score can be used for clinical decision support, such as determining whether to defer intervention or treatment, to recommend preventive check-ups for at-risk patients, to recommend increased visit frequency, to recommend increased testing, and to recommend intervention. The BDAS score can also be useful for therapeutic selection, determining response to treatment, adjustment and dosing of treatment, monitoring ongoing therapeutic efficiency, monitoring therapy withdrawal, and indication for change in therapeutic regimen.

In some embodiments of the present teachings, the BDAS score can be used to aid in the diagnosis of inflammatory disease, and in the determination of the severity of inflammatory disease. The BDAS score can also be used for determining the future status of intervention such as, for example in RA, determining the prognosis of future joint erosion with or without treatment. Certain embodiments of the present teachings can be tailored to a specific treatment or a combination of treatments. X-ray is currently considered the gold standard for assessment of disease progression, but it has limited capabilities since subjects may have long periods of active symptomatic disease while radiographs remain normal or show only nonspecific changes. Conversely, subjects who seem to have quiescent disease (subclinical disease) may slowly progress over time, undetected clinically until significant radiographic progression has occurred. If subjects with a high likelihood of disease progression could be identified in advance, the opportunity for early aggressive treatment could result in much more effective disease outcomes. See, e.g., M. Weinblatt et al., *N. Engl. J. Med.* 1999, 340:253-259.

Systems for Implementing Disease Activity Tests

Tests for measuring disease activity according to various embodiments of the present teachings can be implemented on a variety of systems typically used for obtaining test results, such as results from immunological or nucleic acid detection assays. Such systems may comprise modules that automate sample preparation, that automate testing such as measuring biomarker levels, that facilitate testing of multiple samples, and/or are programmed to assay the same test or different tests on each sample. In some embodiments, the testing system comprises one or more of a sample preparation module, a clinical chemistry module, and an immunoassay module on one platform. Testing systems are typically designed such that they also comprise modules to collect, store, and track results, such as by connecting to and utilizing a database residing on hardware. Examples of these modules include physical and electronic data storage devices as are well-known in the art, such as a hard drive, flash memory, and magnetic tape. Test systems also generally comprise a module for reporting and/or visualizing results. Some examples of reporting modules include a visible display or graphical user interface, links to a database, a printer, etc. See section Machine-readable storage medium, below.

One embodiment of the present invention comprises a system for determining the inflammatory disease activity of a subject. In some embodiments, the system employs a module for applying a formula to an input comprising the measured levels of biomarkers in a panel, as described herein, and outputting a score. In some embodiments, the measured biomarker levels are test results, which serve as inputs to a computer that is programmed to apply the formula. The system may comprise other inputs in addition to or in combination with biomarker results in order to derive an output score; e.g., one or more clinical parameters such as therapeutic regimen, TJC, SJC, morning stiffness, arthritis of three or more joint areas, arthritis of hand joints, symmetric arthritis, rheumatoid nodules, radiographic changes and other imaging, gender/sex, age, race/ethnicity, disease duration, height, weight, body-mass index, family history, CCP status, RF status, ESR, smoker/non-smoker, etc. In some embodiments the system can apply a formula to biomarker level inputs, and then output a disease activity score that can then be analyzed in conjunction with other inputs such as other clinical parameters. In other embodiments, the system is designed to apply a formula to the biomarker and non-biomarker inputs (such as clinical parameters) together, and then report a composite output disease activity index.

A number of testing systems are presently available that could be used to implement various embodiments of the present teachings. See, for example, the ARCHITECT series of integrated immunochemistry systems—high-throughput, automated, clinical chemistry analyzers (ARCHITECT is a registered trademark of Abbott Laboratories, Abbott Park, Ill. 60064). See C. Wilson et al., "Clinical Chemistry Analyzer Sub-System Level Performance," American Association for Clinical Chemistry Annual Meeting, Chicago, Ill., Jul. 23-27, 2006; and, H J Kisner, "Product development: the making of the Abbott ARCHITECT," *Clin. Lab. Manage. Rev.* 1997 November-December, 11(6):419-21; A. Ognibene et al., "A new modular chemiluminescence immunoassay analyzer evaluated," *Clin. Chem. Lab. Med.* 2000 March, 38(3):251-60; J W Park et al., "Three-year experience in using total laboratory automation system," *Southeast Asian J. Trop. Med. Public Health* 2002, 33 Suppl 2:68-73; D. Pauli et al., "The Abbott Architect c8000: analytical performance and productivity characteristics of a new analyzer applied to general chemistry testing," Clin. Lab. 2005, 51(1-2):31-41.

Another testing system useful for embodiments of the present teachings is the VITROS system (VITROS is a registered trademark of Johnson & Johnson Corp., New Brunswick, N.J.)—an apparatus for chemistry analysis that is used to generate test results from blood and other body fluids for laboratories and clinics. Another testing system is the DIMENSION system (DIMENSION is a registered trademark of Dade Behring Inc., Deerfield Ill.)—a system for the analysis of body fluids, comprising computer software and hardware for operating the analyzers, and analyzing the data generated by the analyzers.

The testing required for various embodiments of the present teachings, e.g. measuring biomarker levels, can be performed by laboratories such as those certified under the Clinical Laboratory Improvement Amendments (42 U.S.C. Section 263(a)), or by laboratories certified under any other federal or state law, or the law of any other country, state or province that governs the operation of laboratories that analyze samples for clinical purposes. Such laboratories include, for example, Laboratory Corporation of America, 358 South Main Street, Burlington, N.C. 27215 (corporate headquarters); Quest Diagnostics, 3 Giralda Farms, Madison, N.J. 07940 (corporate headquarters); and other reference and clinical chemistry laboratories.

Kits

Other embodiments of the present teachings comprise biomarker detection reagents packaged together in the form of a kit for conducting any of the assays of the present teachings. In certain embodiments, the kits comprise oligonucleotides that specifically identify one or more biomarker nucleic acids based on homology and/or complementarity with biomarker nucleic acids. The oligonucleotide sequences may correspond to fragments of the biomarker nucleic acids. For example, the oligonucleotides can be more than 200, 200, 150, 100, 50, 25, 10, or fewer than 10 nucleotides in length. In other embodiments, the kits comprise antibodies to proteins encoded by the biomarker nucleic acids. The kits of the present teachings can also comprise aptamers. The kit can contain in separate containers a nucleic acid or antibody (the antibody either bound to a solid matrix, or packaged separately with reagents for binding to a matrix), control formulations (positive and/or negative), and/or a detectable label, such as but not limited to fluorescein, green fluorescent protein, rhodamine, cyanine dyes, Alexa dyes, luciferase, and radiolabels, among others. Instructions for carrying out the assay, including, optionally, instructions for generating a BDAS score, can be included in the kit; e.g., written, tape, VCR, or CD-ROM. The assay can for example be in the form of a Northern hybridization or a sandwich ELISA as known in the art.

In some embodiments of the present teachings, biomarker detection reagents can be immobilized on a solid matrix, such as a porous strip, to form at least one biomarker detection site. In some embodiments, the measurement or detection region of the porous strip can include a plurality of sites containing a nucleic acid. In some embodiments, the test strip can also contain sites for negative and/or positive controls. Alternatively, control sites can be located on a separate strip from the test strip. Optionally, the different detection sites can contain different amounts of immobilized nucleic acids, e.g., a higher amount in the first detection site and lesser amounts in subsequent sites. Upon the addition of test sample, the number of sites displaying a detectable signal provides a quantitative indication of the amount of biomarker present in the sample. The detection sites can be configured in any suitably detectable shape and can be, e.g., in the shape of a bar or dot spanning the width of a test strip.

In other embodiments of the present teachings, the kit can contain a nucleic acid substrate array comprising one or more nucleic acid sequences. The nucleic acids on the array specifically identify one or more nucleic acid sequences represented by the BDAS markers. In various embodiments, the expression of one or more of the sequences represented by the BDAS markers can be identified by virtue of binding to the array. In some embodiments the substrate array can be on a solid substrate, such as what is known as a "chip." See, e.g., U.S. Pat. No. 5,744,305. In some embodiments the substrate array can be a solution array; e.g., xMAP (Luminex, Austin, Tex.), Cyvera (Illumina, San Diego, Calif.), RayBio Antibody Arrays (RayBiotech, Inc., Norcross, Ga.), CellCard (Vitra Bioscience, Mountain View, Calif.) and Quantum Dots' Mosaic (Invitrogen, Carlsbad, Calif.).

Machine-Readable Storage Medium

A machine-readable storage medium can comprise, for example, a data storage material that is encoded with machine-readable data or data arrays. The data and machine-readable storage medium are capable of being used for a variety of purposes, when using a machine programmed with instructions for using said data. Such purposes include, without limitation, storing, accessing and manipulating information relating to the inflammatory disease activity of a subject or population over time, or disease activity in response to inflammatory disease treatment, or for drug discovery for inflammatory disease, etc. Data comprising measurements of the biomarkers of the present teachings, and/or the evaluation of disease activity or disease state from these biomarkers, can be implemented in computer programs that are executing on programmable computers, which comprise a processor, a data storage system, one or more input devices, one or more output devices, etc. Program code can be applied to the input data to perform the functions described herein, and to generate output information. This output information can then be applied to one or more output devices, according to methods well-known in the art. The computer can be, for example, a personal computer, a microcomputer, or a workstation of conventional design.

The computer programs can be implemented in a high-level procedural or object-oriented programming language, to communicate with a computer system such as for example, the computer system illustrated in FIG. 2. The programs can also be implemented in machine or assembly language. The programming language can also be a compiled or interpreted language. Each computer program can be stored on storage media or a device such as ROM, magnetic diskette, etc., and can be readable by a programmable computer for configuring and operating the computer when the storage media or device is read by the computer to perform the described procedures. Any health-related data management systems of the present teachings can be considered to be implemented as a computer-readable storage medium, configured with a computer program, where the storage medium causes a computer to operate in a specific manner to perform various functions, as described herein.

The biomarkers disclosed herein can be used to generate a "subject biomarker profile" taken from subjects who have inflammatory disease. The subject biomarker profiles can then be compared to a reference biomarker profile, in order to diagnose or identify subjects with inflammatory disease, to monitor the progression or rate of progression of inflammatory disease, or to monitor the effectiveness of treatment for inflammatory disease. The biomarker profiles, reference and subject, of embodiments of the present teachings can be contained in a machine-readable medium, such as analog tapes like those readable by a CD-ROM or USB flash media, among others. Such machine-readable media can also contain additional test results, such as measurements of clinical parameters and clinical assessments. The machine-readable media can also comprise subject information; e.g., the subject's medical or family history. The machine-readable media can also contain information relating to other disease activity algorithms and computed scores or indices, such as those described herein.

EXAMPLES

Aspects of the present teachings can be further understood in light of the following examples, which should not be construed as limiting the scope of the present teachings in any way.

The practice of the present teachings employ, unless otherwise indicated, conventional methods of protein chemistry, biochemistry, recombinant DNA techniques and pharmacology, within the skill of the art. Such techniques are explained fully in the literature. See, e.g., T. Creighton, *Proteins: Structures and Molecular Properties*, 1993, W. Freeman and Co.; A. Lehninger, *Biochemistry*, Worth Publishers, Inc. (current addition); J. Sambrook et al., *Molecular Cloning: A Laboratory Manual*, 2nd Edition, 1989; *Methods In Enzymology*, S. Colowick and N. Kaplan, eds., Academic Press, Inc.; *Remington's Pharmaceutical Sciences*, 18th Edition, 1990, Mack Publishing Company, Easton, Pa.; Carey and Sundberg, *Advanced Organic Chemistry*, Vols. A and B, 3rd Edition, 1992, Plenum Press.

The practice of the present teachings also employ, unless otherwise indicated, conventional methods of statistical analysis, within the skill of the art. Such techniques are explained fully in the literature. See, e.g., J. Little and D. Rubin, *Statistical Analysis with Missing Data*, 2nd Edition 2002, John Wiley and Sons, Inc., NJ; M. Pepe, *The Statistical Evaluation of Medical Tests for Classification and Prediction* (*Oxford Statistical Science Series*) 2003, Oxford University Press, Oxford, UK; X. Zhoue et al., *Statistical Methods in Diagnostic Medicine* 2002, John Wiley and Sons, Inc., NJ; T. Hastie et. al, *The Elements of Statistical Learning: Data Mining, Inference, and Prediction*, Second Edition 2009, Springer, N.Y.; W. Cooley and P. Lohnes, *Multivariate procedures for the behavioral science* 1962, John Wiley and Sons, Inc. NY; E. Jackson, *A User's Guide to Principal Components* 2003, John Wiley and Sons, Inc., NY.

Example 1: Deriving a BDAS Score

This example demonstrates a method of deriving a Biomarker Disease Activity Score (BDAS) score, based on a dataset of quantitative data for biomarkers. In this example, a BDAS score is determined from the biomarker data using an interpretation function that is based on a set of predictive models.

Samples from 144 rheumatoid arthritis (RA) patients were assayed for 316 proteins with the Myriad/RBM DiscoveryMAP® version 3.3 to discover biomarkers useful for assessing RA disease activity. Patient samples were selected from The Index for Rheumatoid Arthritis measurement (InFoRM) cohort. The InFoRM study is a large multi-center observational study of the North American RA population. Patients were recruited between April and September 2009 from 25 sites in the U.S. and Canada. Inclusion criteria were: age>18 with a diagnosis of RA made by a board-certified rheumatologist. Patients concurrently enrolled in a therapeutic drug trial involving a biologic agent and a placebo arm were excluded. The average age of the patients was 58.9 years (range 20-91), and 76% were female. Clinical data, including clinical disease activity measures in current clinical use, were used as comparators for correlations with disease activity. The disease activity measures were physician's global analysis, patient's global assessment, swollen joint counts, tender joint counts, MDHAQ, CDAI, SDAI, RAPID-3 and DAS28ESR. Comparison against DAS28ESR is illustrated in FIG. 1. DAS28ESR was used as the CRP concentration is used in the calculation of DAS28CRP. DAS28CRP and DAS28ESR were highly correlated (Pearson R>0.95).

Biomarker concentrations were correlated (Spearman non-parametric) with each of the clinical disease activity measures listed above. Biomarkers with p-values>0.05 were excluded from further analysis.

The biomarkers most closely correlated to DASESR are shown in Table 1.

TABLE 1

| Biomarker | Spearman rho correlation | Probability |
|---|---|---|
| Serum Amyloid P-Component (SAP) | 0.39 | 1.07E-06 |
| Cathepsin D | 0.39 | 1.25E-06 |
| Chemerin | 0.38 | 2.71E-06 |
| Alpha-1-Microglobulin (A1Micro) | 0.37 | 6.20E-06 |
| Haptoglobin | 0.37 | 7.52E-06 |
| Pigment Epithelium Derived Factor (PEDF) | 0.36 | 9.63E-06 |
| Clusterin (CLU) | 0.34 | 3.14E-05 |
| Tissue type Plasminogen activator (tPA) | 0.31 | 0.00012 |
| Monocyte Chemotactic Protein 4 (MCP-4) | 0.31 | 0.00017 |
| Alpha-1-acid glycoprotein 1 (AGP-1) | 0.30 | 0.00022 |
| C-Peptide | 0.30 | 0.00022 |
| Complement Factor H (CFH) | 0.30 | 0.00025 |
| C-Reactive Protein (CRP) | 0.30 | 0.00025 |
| Pulmonary and Activation-Regulated Chemokine (PARC) | 0.29 | 0.00053 |
| Growth-Regulated alpha protein (GRO-alpha) | 0.28 | 0.00057 |
| Sex Hormone-Binding Globulin (SHBG) | −0.28 | 0.00085 |
| Matrix Metalloproteinase-7 (MMP-7) | 0.27 | 0.0012 |
| Growth/differentiation factor 15 (GDF-15) | 0.26 | 0.0014 |
| Fibroblast Growth Factor 21 (FGF-21) | 0.26 | 0.0015 |
| Angiopoietin-related protein 3 (ANGPTL3) | 0.26 | 0.0015 |
| Hemopexin | 0.26 | 0.0016 |
| FASLG Receptor (FAS) | 0.26 | 0.0018 |
| Receptor for advanced glycosylation end products (RAGE) | −0.26 | 0.0019 |
| CD5 Antigen-like (CD5L) | 0.26 | 0.0019 |
| Endoglin | −0.25 | 0.0024 |
| von Willebrand Factor (vWF) | 0.25 | 0.0025 |
| Chemokine CC-4 (HCC-4) | 0.24 | 0.0031 |
| Alpha-1-Antichymotrypsin (AACT) | 0.24 | 0.0033 |
| Protein DJ-1 (DJ-1) | 0.23 | 0.0047 |
| Cystatin-B | 0.23 | 0.0060 |
| Alpha-Fetoprotein (AFP) | −0.28 | 0.0082 |
| Thrombin-Activatable Fibrinolysis (TAFI) | 0.22 | 0.0085 |
| Immunoglobulin A (IgA) | 0.22 | 0.0089 |
| Epithelial-Derived Neutrophil-Activating Protein 78 (ENA-78) | 0.22 | 0.0091 |

TABLE 1-continued

| Biomarker | Spearman rho correlation | Probability |
|---|---|---|
| Vitamin K-Dependent Protein S (VKDPS) | 0.22 | 0.0093 |
| CD 40 antigen (CD40) | 0.21 | 0.0099 |
| Apolipoprotein C-III (Apo C-III) | 0.21 | 0.011 |
| Interleukin-1 receptor antagonist (IL-1ra) | 0.22 | 0.011 |
| Ficolin-3 | 0.21 | 0.013 |
| Peroxiredoxin-4 (Prx-IV) | 0.21 | 0.014 |
| ST2 | 0.20 | 0.014 |
| Sortilin | 0.20 | 0.015 |
| Tumor necrosis factor ligand superfamily member 12 (Tweak) | −0.20 | 0.016 |
| Phosphoserine Aminotransferase (PSAT) | 0.20 | 0.017 |
| Heparin-Binding EGF-Like Growth Factor (HB-EGF) | 0.20 | 0.019 |
| Interleukin-8 (IL-8) | 0.19 | 0.024 |
| Beta-2-Microglobulin (B2M) | 0.19 | 0.026 |
| Apolipoprotein E (Apo E) | 0.19 | 0.026 |
| Urokinase-type Plasminogen Activator (uPA) | −0.19 | 0.028 |
| Adrenomedullin (ADM) | 0.18 | 0.031 |
| Urokinase-type plasminogen activator receptor (uPAR) | 0.18 | 0.031 |
| Tetranectin | −0.18 | 0.031 |
| E-Selectin | 0.18 | 0.033 |
| Monokine Induced by Gamma Interferon (MIG) | 0.18 | 0.034 |
| Glucagon-like Peptide 1, total (GLP-1 total) | 0.18 | 0.035 |
| Interleukin-12 Subunit p40 (IL-12p40) | 0.18 | 0.036 |
| Cartilage Oligomeric Matrix Protein (COMP) | 0.17 | 0.036 |
| Apolipoprotein H (Apo H) | 0.17 | 0.038 |
| Factor VII | 0.17 | 0.039 |
| Interferon-inducible T-cell alpha chemoattractant (ITAC) | 0.19 | 0.041 |
| Antileukoproteinase (ALP) | 0.17 | 0.042 |
| Thymus and activation-regulated chemokine (TARC) | 0.17 | 0.044 |
| Plasminogen Activator Inhibitor 1 (PAI-1) | 0.17 | 0.044 |
| Interleukin-15 (IL-15) | 0.22 | 0.046 |
| Ceruloplasmin | 0.17 | 0.046 |
| Complement Factor H - Related Protein 1 (CFHR1) | 0.17 | 0.046 |

The biomarkers most closely correlated to CDAI are shown in Table 2.

TABLE 2

| Biomarker | Spearman rho correlation | Probability |
|---|---|---|
| Serum Amyloid P-Component (SAP) | 0.35 | 2.21E−05 |
| Pigment Epithelium Derived Factor (PEDF) | 0.32 | 8.54E−05 |
| Cathepsin D | 0.32 | 8.74E−05 |
| C-Peptide | 0.29 | 0.0004 |
| Alpha-1-Microglobulin (A1Micro) | 0.27 | 0.0011 |
| CD5 Antigen-like (CD5L) | 0.26 | 0.0015 |
| Tissue type Plasminogen activator (tPA) | 0.25 | 0.0024 |
| FASLG Receptor (FAS) | 0.26 | 0.0025 |
| Sex Hormone-Binding Globulin (SHBG) | −0.25 | 0.0025 |
| Chemerin | 0.25 | 0.0028 |
| Protein DJ-1 (DJ-1) | 0.24 | 0.0038 |
| Growth/differentiation factor 15 (GDF-15) | 0.24 | 0.0039 |
| Fibroblast Growth Factor 21 (FGF-21) | 0.23 | 0.0047 |

TABLE 2-continued

| Biomarker | Spearman rho correlation | Probability |
|---|---|---|
| Receptor for advanced glycosylation end products (RAGE) | −0.23 | 0.0056 |
| Clusterin (CLU) | 0.23 | 0.0062 |
| Alpha-Fetoprotein (AFP) | −0.28 | 0.0079 |
| Monocyte Chemotactic Protein 4 (MCP-4) | 0.22 | 0.0081 |
| ST2 | 0.21 | 0.0097 |
| von Willebrand Factor (vWF) | 0.21 | 0.011 |
| Complement Factor H (CFH) | 0.21 | 0.013 |
| Haptoglobin | 0.21 | 0.014 |
| Chemokine CC-4 (HCC-4) | 0.20 | 0.016 |
| Ferritin (FRTN) | 0.20 | 0.016 |
| Ficolin-3 | 0.20 | 0.019 |
| Urokinase-type Plasminogen Activator (uPA) | −0.20 | 0.019 |
| Glucagon-like Peptide 1, total (GLP-1 total) | 0.20 | 0.022 |
| Alpha-1-acid glycoprotein 1 (AGP-1) | 0.19 | 0.022 |
| Interleukin-15 (IL-15) | 0.25 | 0.023 |
| Matrix Metalloproteinase-7 (MMP-7) | 0.19 | 0.025 |
| Immunoglobulin A (IgA) | 0.19 | 0.026 |
| Thrombin-Activatable Fibrinolysis (TAFI) | 0.18 | 0.031 |
| Tetranectin | −0.18 | 0.032 |
| Endoglin | −0.18 | 0.032 |
| Tumor necrosis factor ligand superfamily member 12 (Tweak) | −0.18 | 0.033 |
| Complement Factor H - Related Protein 1 (CFHR1) | 0.18 | 0.033 |
| Peroxiredoxin-4 (Prx-IV) | 0.18 | 0.035 |
| Cystatin-B | 0.17 | 0.040 |
| Alpha-1-Antichymotrypsin (AACT) | 0.17 | 0.041 |
| Phosphoserine Aminotransferase (PSAT) | 0.17 | 0.042 |
| Pancreatic Polypeptide (PPP) | 0.17 | 0.042 |
| C-Reactive Protein (CRP) | 0.16 | 0.050 |

The biomarkers most closely correlated to SDAI are shown in Table 3.

TABLE 3

| Biomarker | Spearman rho correlation | Probability |
|---|---|---|
| Serum Amyloid P-Component (SAP) | 0.37 | 4.28E−06 |
| Cathepsin D | 0.33 | 4.08E−05 |
| Pigment Epithelium Derived Factor (PEDF) | 0.33 | 5.54E−05 |
| C-Peptide | 0.29 | 0.00035 |
| Alpha-1-Microglobulin (A1Micro) | 0.29 | 0.00048 |
| Chemerin | 0.28 | 0.00078 |
| CD5 Antigen-like (CD5L) | 0.26 | 0.0013 |
| Tissue type Plasminogen activator (tPA) | 0.26 | 0.0015 |
| FASLG Receptor (FAS) | 0.26 | 0.0021 |
| Growth/differentiation factor 15 (GDF-15) | 0.25 | 0.0025 |
| Fibroblast Growth Factor 21 (FGF-21) | 0.25 | 0.0028 |
| Sex Hormone-Binding Globulin (SHBG) | −0.25 | 0.0030 |
| Clusterin (CLU) | 0.24 | 0.0036 |
| Receptor for advanced glycosylation end products (RAGE) | −0.24 | 0.0043 |
| Haptoglobin | 0.24 | 0.0044 |
| Complement Factor H (CFH) | 0.23 | 0.0047 |
| Alpha-Fetoprotein (AFP) | −0.30 | 0.0048 |
| Alpha-1-acid glycoprotein 1 (AGP-1) | 0.23 | 0.0049 |
| Protein DJ-1 (DJ-1) | 0.23 | 0.0050 |
| von Willebrand Factor (vWF) | 0.23 | 0.0054 |
| Monocyte Chemotactic Protein 4 (MCP-4) | 0.23 | 0.0055 |

TABLE 3-continued

| Biomarker | Spearman rho correlation | Probability |
|---|---|---|
| ST2 | 0.22 | 0.0070 |
| C-Reactive Protein (CRP) | 0.22 | 0.0083 |
| Chemokine CC-4 (HCC-4) | 0.22 | 0.0085 |
| Alpha-1-Antichymotrypsin (AACT) | 0.20 | 0.015 |
| Urokinase-type Plasminogen Activator (uPA) | −0.21 | 0.015 |
| Ferritin (FRTN) | 0.20 | 0.018 |
| Thrombin-Activatable Fibrinolysis (TAFI) | 0.19 | 0.019 |
| Matrix Metalloproteinase-7 (MMP-7) | 0.19 | 0.020 |
| Glucagon-like Peptide 1, total (GLP-1 total) | 0.20 | 0.021 |
| Tumor necrosis factor ligand superfamily member 12 (Tweak) | −0.19 | 0.022 |
| Ficolin-3 | 0.19 | 0.022 |
| Interleukin-15 (IL-15) | 0.25 | 0.024 |
| Cystatin-B | 0.19 | 0.024 |
| Endoglin | −0.19 | 0.025 |
| Pulmonary and Activation-Regulated Chemokine (PARC) | 0.18 | 0.029 |
| Growth-Regulated alpha protein (GRO-alpha) | 0.18 | 0.029 |
| Tetranectin | −0.18 | 0.031 |
| Complement Factor H - Related Protein 1 (CFHR1) | 0.18 | 0.032 |
| Peroxiredoxin-4 (Prx-IV) | 0.18 | 0.032 |
| Immunoglobulin A (IgA) | 0.18 | 0.034 |
| Apolipoprotein C-III (Apo C-III) | 0.17 | 0.037 |
| Hemopexin | 0.17 | 0.041 |
| Pancreatic Polypeptide (PPP) | 0.17 | 0.042 |
| Heat-Shock protein 70 (HSP-70) | 0.17 | 0.045 |
| Phosphoserine Aminotransferase (PSAT) | 0.17 | 0.049 |
| Transferrin receptor protein 1 (TFR1) | 0.16 | 0.050 |

The biomarkers most closely correlated to RAPID 3 are shown in Table 4.

TABLE 4

| Biomarker | Spearman rho correlation | Probability |
|---|---|---|
| Pigment Epithelium Derived Factor (PEDF) | 0.37 | 1.02E−05 |
| Serum Amyloid P-Component (SAP) | 0.35 | 3.34E−05 |
| Growth/differentiation factor 15 (GDF-15) | 0.32 | 0.00012 |
| Chemerin | 0.32 | 0.00018 |
| Alpha-1-Microglobulin (A1Micro) | 0.31 | 0.00021 |
| Alpha-1-Antichymotrypsin (AACT) | 0.31 | 0.00021 |
| Alpha-1-acid glycoprotein 1 (AGP-1) | 0.30 | 0.00032 |
| Cathepsin D | 0.30 | 0.00043 |
| Sex Hormone-Binding Globulin (SHBG) | −0.29 | 0.00064 |
| Cystatin-B | 0.29 | 0.00074 |
| C-Reactive Protein (CRP) | 0.27 | 0.0015 |
| Haptoglobin | 0.26 | 0.0020 |
| Hemopexin | 0.26 | 0.0025 |
| Tamm-Horsfall Urinary Glycoprotein (THP) | −0.26 | 0.0026 |
| Tetranectin | −0.25 | 0.0029 |
| C-Peptide | 0.25 | 0.0030 |
| Antileukoproteinase (ALP) | 0.25 | 0.0030 |
| Complement Factor H (CFH) | 0.24 | 0.0039 |
| Tissue type Plasminogen activator (tPA) | 0.24 | 0.0039 |
| Urokinase-type plasminogen activator receptor (uPAR) | 0.24 | 0.0041 |
| Tenascin-C (TN-C) | 0.24 | 0.0049 |
| CD5 Antigen-like (CD5L) | 0.24 | 0.0053 |
| von Willebrand Factor (vWF) | 0.24 | 0.0056 |

TABLE 4-continued

| Biomarker | Spearman rho correlation | Probability |
|---|---|---|
| FASLG Receptor (FAS) | 0.24 | 0.0063 |
| Receptor for advanced glycosylation end products (RAGE) | −0.23 | 0.0071 |
| Urokinase-type Plasminogen Activator (uPA) | −0.23 | 0.0077 |
| Phosphoserine Aminotransferase (PSAT) | 0.23 | 0.0096 |
| Chromogranin-A (CgA) | 0.22 | 0.011 |
| Clusterin (CLU) | 0.22 | 0.011 |
| Interferon-inducible T-cell alpha chemoattractant (ITAC) | 0.24 | 0.011 |
| Pepsinogen I (PGI) | 0.23 | 0.011 |
| Peroxiredoxin-4 (Prx-IV) | 0.22 | 0.011 |
| Hepatocyte Growth Factor (HGF) | 0.21 | 0.012 |
| Thrombin-Activatable Fibrinolysis (TAFI) | 0.21 | 0.016 |
| Adrenomedullin (ADM) | 0.20 | 0.018 |
| T-Cell-Specific Protein RANTES (RANTES) | 0.20 | 0.021 |
| Apolipoprotein C-III (Apo C-III) | 0.19 | 0.024 |
| Fibroblast Growth Factor 21 (FGF-21) | 0.19 | 0.025 |
| Tumor necrosis factor receptor 2 (TNFR2) | 0.20 | 0.026 |
| ST2 | 0.19 | 0.029 |
| Macrophage Colony-Stimulating Factor 1 (M-CSF) | 0.20 | 0.029 |
| Beta Amyloid 1-40 (AB-40) | 0.19 | 0.031 |
| Tumor necrosis factor ligand superfamily member 12 (Tweak) | −0.18 | 0.032 |
| Cystatin-C | 0.18 | 0.033 |
| Interleukin-15 (IL-15) | 0.23 | 0.035 |
| Tissue Inhibitor of Metalloproteinases 3 (TIMP-3) | 0.18 | 0.038 |
| Insulin-like Growth Factor Binding Protein 4 (IGFBP4) | 0.18 | 0.040 |
| Glucagon-like Peptide 1, total (GLP-1 total) | 0.18 | 0.040 |
| Gastric inhibitory polypeptide (GIP) | 0.18 | 0.042 |
| Midkine | 0.17 | 0.046 |
| Angiogenin | 0.17 | 0.047 |

The biomarkers most closely correlated to Tender Joint Counts are shown in Table 5.

TABLE 5

| Biomarker | Spearman rho correlation | Probability |
|---|---|---|
| Cathepsin D | 0.26 | 0.0019 |
| Sex Hormone-Binding Globulin (SHBG) | −0.26 | 0.0020 |
| Serum Amyloid P-Component (SAP) | 0.23 | 0.0046 |
| Pigment Epithelium Derived Factor (PEDF) | 0.23 | 0.0050 |
| C-Peptide | 0.21 | 0.012 |
| Receptor for advanced glycosylation end products (RAGE) | −0.20 | 0.014 |
| Chemerin | 0.20 | 0.014 |
| FASLG Receptor (FAS) | 0.21 | 0.015 |
| Interleukin-15 (IL-15) | 0.26 | 0.018 |
| Monocyte Chemotactic Protein 4 (MCP-4) | 0.19 | 0.020 |
| Tissue type Plasminogen activator (tPA) | 0.19 | 0.021 |
| Chemokine CC-4 (HCC-4) | 0.19 | 0.022 |
| Phosphoserine Aminotransferase (PSAT) | 0.19 | 0.027 |
| Protein DJ-1 (DJ-1) | 0.18 | 0.028 |
| Tetranectin | −0.18 | 0.028 |
| Haptoglobin | 0.18 | 0.034 |
| Alpha-Fetoprotein (AFP) | −0.21 | 0.045 |
| E-Selectin | 0.16 | 0.050 |

The biomarkers most closely correlated to Swollen Joint Counts are shown in Table 6.

TABLE 6

| Biomarker | Spearman rho correlation | Probability |
|---|---|---|
| Cathepsin D | 0.32 | 7.26E−05 |
| Monocyte Chemotactic Protein 4 (MCP-4) | 0.31 | 2.10E−04 |
| C-Peptide | 0.30 | 0.00026 |
| CD5 Antigen-like (CD5L) | 0.30 | 0.00027 |
| Serum Amyloid P-Component (SAP) | 0.29 | 0.00035 |
| Pigment Epithelium Derived Factor (PEDF) | 0.29 | 0.00045 |
| Clusterin (CLU) | 0.27 | 0.0011 |
| Protein DJ-1 (DJ-1) | 0.26 | 0.0018 |
| Fibroblast Growth Factor 21 (FGF-21) | 0.25 | 0.0021 |
| Alpha-1-Microglobulin (A1Micro) | 0.25 | 0.0022 |
| Ferritin (FRTN) | 0.25 | 0.0025 |
| Stem Cell Factor (SCF) | 0.24 | 0.0036 |
| Pulmonary and Activation-Regulated Chemokine (PARC) | 0.23 | 0.0046 |
| Alpha-Fetoprotein (AFP) | −0.29 | 0.0052 |
| Complement Factor H (CFH) | 0.23 | 0.0053 |
| Tissue type Plasminogen activator (tPA) | 0.23 | 0.0065 |
| Ficolin-3 | 0.23 | 0.0067 |
| Sortilin | 0.22 | 0.0076 |
| Interleukin-8 (IL-8) | 0.22 | 0.0078 |
| Matrix Metalloproteinase-7 (MMP-7) | 0.22 | 0.0082 |
| Chemokine CC-4 (HCC-4) | 0.22 | 0.0082 |
| Growth/differentiation factor 15 (GDF-15) | 0.21 | 0.0097 |
| Thrombin-Activatable Fibrinolysis (TAFI) | 0.21 | 0.011 |
| Myeloid Progenitor Inhibitory Factor 1 (MPIF-1) | 0.21 | 0.013 |
| Osteoprotegerin (OPG) | 0.20 | 0.014 |
| CD 40 antigen (CD40) | 0.20 | 0.014 |
| Endoglin | −0.20 | 0.015 |
| Alpha-1-acid glycoprotein 1 (AGP-1) | 0.20 | 0.017 |
| Cartilage Oligomeric Matrix Protein (COMP) | 0.20 | 0.018 |
| Complement Factor H-Related Protein 1 (CFHR1) | 0.20 | 0.019 |
| FASLG Receptor (FAS) | 0.20 | 0.022 |
| Monocyte Chemotactic Protein 2 (MCP-2) | 0.19 | 0.022 |
| Chemerin | 0.19 | 0.024 |
| von Willebrand Factor (vWF) | 0.19 | 0.024 |
| Serotransferrin (Transferrin) | −0.19 | 0.024 |
| Glucagon-like Peptide 1, total (GLP-1 total) | 0.19 | 0.026 |
| Interleukin-12 Subunit p40 (IL-12p40) | 0.18 | 0.030 |
| Pancreatic Polypeptide (PPP) | 0.18 | 0.030 |
| Tumor necrosis factor ligand superfamily member 12 (Tweak) | −0.18 | 0.033 |
| Insulin-like Growth Factor-Binding Protein 1 (IGFBP-1) | −0.19 | 0.033 |
| Immunoglobulin A (IgA) | 0.18 | 0.034 |
| Vitamin K-Dependent Protein S (VKDPS) | 0.18 | 0.034 |
| Apolipoprotein E (Apo E) | 0.18 | 0.035 |
| Transferrin receptor protein 1 (TFR1) | 0.17 | 0.036 |
| Hepatocyte Growth Factor receptor (HGF receptor) | −0.17 | 0.038 |
| E-Selectin | 0.17 | 0.043 |
| Growth-Regulated alpha protein (GRO-alpha) | 0.17 | 0.047 |
| Heat-Shock protein 70 (HSP-70) | 0.17 | 0.047 |
| C-Reactive Protein (CRP) | 0.17 | 0.048 |
| ST2 | 0.16 | 0.048 |
| Tamm-Horsfall Urinary Glycoprotein (THP) | −0.16 | 0.049 |

The biomarkers most closely correlated to Physicians Global Assessment are shown in Table 7.

TABLE 7

| Biomarker | Spearman rho correlation | Probability |
|---|---|---|
| Serum Amyloid P-Component (SAP) | 0.34 | 3.48E−05 |
| Cathepsin D | 0.31 | 0.00016 |
| Pigment Epithelium Derived Factor (PEDF) | 0.31 | 0.00017 |
| Sex Hormone-Binding Globulin (SHBG) | −0.30 | 0.00025 |
| Alpha-1-acid glycoprotein 1 (AGP-1) | 0.29 | 0.00035 |
| CD5 Antigen-like (CD5L) | 0.29 | 0.00048 |
| Alpha-1-Microglobulin (A1Micro) | 0.29 | 0.00052 |
| Alpha-1-Antichymotrypsin (AACT) | 0.28 | 0.00081 |
| Growth/differentiation factor 15 (GDF-15) | 0.27 | 0.0010 |
| FASLG Receptor (FAS) | 0.26 | 0.0023 |
| Tissue type Plasminogen activator (tPA) | 0.25 | 0.0023 |
| von Willebrand Factor (vWF) | 0.25 | 0.0023 |
| C-Reactive Protein (CRP) | 0.25 | 0.0024 |
| Chemerin | 0.25 | 0.0025 |
| Receptor for advanced glycosylation end products (RAGE) | −0.25 | 0.0029 |
| C-Peptide | 0.25 | 0.0031 |
| Cystatin-B | 0.24 | 0.0034 |
| Phosphoserine Aminotransferase (PSAT) | 0.24 | 0.0043 |
| Tenascin-C (TN-C) | 0.23 | 0.0047 |
| Urokinase-type Plasminogen Activator (uPA) | −0.24 | 0.0050 |
| Tetranectin | −0.23 | 0.0050 |
| Haptoglobin | 0.23 | 0.0052 |
| Complement Factor H (CFH) | 0.23 | 0.0056 |
| Antileukoproteinase (ALP) | 0.23 | 0.0058 |
| Hemopexin | 0.22 | 0.0072 |
| ST2 | 0.22 | 0.0073 |
| Urokinase-type plasminogen activator receptor (uPAR) | 0.22 | 0.0086 |
| Interferon-inducible T-cell alpha chemoattractant (ITAC) | 0.23 | 0.011 |
| Immunoglobulin A (IgA) | 0.21 | 0.012 |
| Clusterin (CLU) | 0.20 | 0.017 |
| Tumor necrosis factor receptor 2 (TNFR2) | 0.20 | 0.018 |
| Pepsinogen I (PGI) | 0.21 | 0.018 |
| Tamm-Horsfall Urinary Glycoprotein (THP) | −0.20 | 0.019 |
| Chromogranin-A (CgA) | 0.20 | 0.021 |
| Gastric inhibitory polypeptide (GIP) | 0.20 | 0.023 |
| Macrophage Colony-Stimulating Factor 1 (M-CSF) | 0.19 | 0.027 |
| Protein DJ-1 (DJ-1) | 0.18 | 0.030 |
| Peroxiredoxin-4 (Prx-IV) | 0.18 | 0.032 |
| Hepatocyte Growth Factor (HGF) | 0.18 | 0.035 |
| Adrenomedullin (ADM) | 0.18 | 0.036 |
| Brain-Derived Neurotrophic Factor (BDNF) | −0.17 | 0.039 |
| Beta Amyloid 1-40 (AB-40) | 0.17 | 0.042 |
| Hepatocyte Growth Factor receptor (HGF receptor) | −0.17 | 0.045 |
| Interleukin-15 (IL-15) | 0.22 | 0.045 |

The biomarkers most closely correlated to the Patients Global Assessment are shown in Table 8.

TABLE 8

| Biomarker | Spearman rho correlation | Probability |
| --- | --- | --- |
| Serum Amyloid P-Component (SAP) | 0.338 | 0.00003 |
| Cathepsin D | 0.309 | 0.00016 |
| Pigment Epithelium Derived Factor (PEDF) | 0.308 | 0.00017 |
| Sex Hormone-Binding Globulin (SHBG) | −0.301 | 0.00025 |
| Alpha-1-acid glycoprotein 1 (AGP-1) | 0.294 | 0.00035 |
| CD5 Antigen-like (CD5L) | 0.288 | 0.00048 |
| Alpha-1-Microglobulin (A1Micro) | 0.286 | 0.0005 |
| Alpha-1-Antichymotrypsin (AACT) | 0.276 | 0.0008 |
| Growth/differentiation factor 15 (GDF-15) | 0.271 | 0.0010 |
| FASLG Receptor (FAS) | 0.259 | 0.0023 |
| Tissue type Plasminogen activator (tPA) | 0.252 | 0.0023 |
| von Willebrand Factor (vWF) | 0.252 | 0.0023 |
| C-Reactive Protein (CRP) | 0.252 | 0.0024 |
| Chemerin | 0.251 | 0.0025 |
| Receptor for advanced glycosylation end products (RAGE) | −0.246 | 0.0029 |
| C-Peptide | 0.246 | 0.0031 |
| Cystatin-B | 0.243 | 0.0034 |
| Phosphoserine Aminotransferase (PSAT) | 0.243 | 0.0043 |
| Tenascin-C (TN-C) | 0.234 | 0.0047 |
| Urokinase-type Plasminogen Activator (uPA) | −0.239 | 0.0050 |
| Tetranectin | −0.232 | 0.0050 |
| Haptoglobin | 0.233 | 0.0052 |
| Complement Factor H (CFH) | 0.230 | 0.0056 |
| Antileukoproteinase (ALP) | 0.229 | 0.0058 |
| Hemopexin | 0.223 | 0.0072 |
| ST2 | 0.223 | 0.0073 |
| Urokinase-type plasminogen activator receptor (uPAR) | 0.218 | 0.0086 |
| Interferon-inducible T-cell alpha chemoattractant (ITAC) | 0.231 | 0.011 |
| Immunoglobulin A (IgA) | 0.210 | 0.012 |
| Clusterin (CLU) | 0.199 | 0.017 |
| Tumor necrosis factor receptor 2 (TNFR2) | 0.205 | 0.018 |
| Pepsinogen I (PGI) | 0.207 | 0.018 |
| Tamm-Horsfall Urinary Glycoprotein (THP) | −0.195 | 0.019 |
| Chromogranin-A (CgA) | 0.196 | 0.021 |
| Gastric inhibitory polypeptide (GIP) | 0.197 | 0.023 |
| Macrophage Colony-Stimulating Factor 1 (M-CSF) | 0.194 | 0.027 |
| Protein DJ-1 (DJ-1) | 0.181 | 0.030 |
| Peroxiredoxin-4 (Prx-IV) | 0.182 | 0.032 |
| Hepatocyte Growth Factor (HGF) | 0.176 | 0.035 |
| Adrenomedullin (ADM) | 0.176 | 0.036 |
| Brain-Derived Neurotrophic Factor (BDNF) | −0.173 | 0.039 |
| Beta Amyloid 1-40 (AB-40) | 0.171 | 0.042 |
| Hepatocyte Growth Factor receptor (HGF receptor) | −0.167 | 0.045 |
| Interleukin-15 (IL-15) | 0.218 | 0.045 |

The biomarkers most closely correlated with MD HAQ are shown in Table 9.

TABLE 9

| Biomarker | Spearman rho correlation | Probability |
| --- | --- | --- |
| Chemerin | 0.31 | 0.0005 |
| Pigment Epithelium Derived Factor (PEDF) | 0.29 | 0.0011 |
| Cathepsin D | 0.28 | 0.0020 |
| Tissue type Plasminogen activator (tPA) | 0.28 | 0.0021 |
| C-Peptide | 0.27 | 0.0024 |
| Alpha-1-Microglobulin (A1Micro) | 0.25 | 0.0055 |
| Serum Amyloid P-Component (SAP) | 0.24 | 0.0065 |
| Sex Hormone-Binding Globulin (SHBG) | −0.24 | 0.0071 |
| Interleukin-6 receptor subunit beta (IL-6R beta) | 0.24 | 0.0075 |
| Matrix Metalloproteinase-7 (MMP-7) | 0.24 | 0.0083 |
| Interleukin-15 (IL-15) | 0.31 | 0.0089 |
| FASLG Receptor (FAS) | 0.23 | 0.012 |
| Peroxiredoxin-4 (Prx-IV) | 0.22 | 0.015 |
| Interleukin-1 receptor antagonist (IL-1ra) | 0.23 | 0.015 |
| Macrophage-Stimulating Protein (MSP) | 0.22 | 0.016 |
| Angiogenin | 0.21 | 0.017 |
| Gastric inhibitory polypeptide (GIP) | 0.22 | 0.018 |
| Alpha-1-acid glycoprotein 1 (AGP-1) | 0.19 | 0.034 |
| CD5 Antigen-like (CD5L) | 0.19 | 0.036 |
| Hepatocyte Growth Factor (HGF) | 0.19 | 0.037 |
| Urokinase-type Plasminogen Activator (uPA) | −0.19 | 0.041 |
| Phosphoserine Aminotransferase (PSAT) | 0.19 | 0.044 |
| Monocyte Chemotactic Protein 1 (MCP-1) | −0.18 | 0.048 |
| T-Cell-Specific Protein RANTES (RANTES) | 0.18 | 0.050 |

Biomarkers that correlate with multiple different clinical disease activity measures are useful for their range several pathological mechanisms. Biomarkers demonstrating significant correlations with DASESR, CDAI, Physicians Global, Tender Joint Counts, Swollen Joint Counts, Patients Global, and MDHAQ are shown in Table 10.

TABLE 10

| Biomarker |
| --- |
| Cathepsin D |
| Serum Amyloid P-Component (SAP) |
| Pigment Epithelium Derived Factor (PEDF) |
| C-Peptide |
| Tissue type Plasminogen activator (tPA) |
| Chemerin |
| FASLG Receptor (FAS) |

Biomarkers that correlate with multiple composite assays such as DASESR, CDAI, and SDAI are shown in Table 11.

TABLE 11

| Biomarker |
| --- |
| Cathepsin D |
| Alpha-1-Microglobulin (A1Micro) |
| Chemerin |
| C-Peptide |

TABLE 11-continued

| Biomarker |
|---|
| Tissue type Plasminogen activator (tPA) |
| Sex Hormone-Binding Globulin (SHBG) |
| Growth/differentiation factor 15 (GDF-15) |
| Haptoglobin |
| CD5 Antigen-like (CD5L) |
| Alpha-1-acid glycoprotein 1 (AGP-1) |
| Clusterin (CLU) |
| FASLG Receptor (FAS) |
| Complement Factor H (CFH) |
| Receptor for advanced glycosylation end products (RAGE) |
| Fibroblast Growth Factor 21 (FGF-21) |
| von Willebrand Factor (vWF) |
| C-Reactive Protein (CRP) |
| Alpha-1-Antichymotrypsin (AACT) |
| Cystatin-B |
| ST2 |
| Thrombin-Activatable Fibrinolysis (TAFI) |
| Urokinase-type Plasminogen Activator (uPA) |
| Tetranectin |
| Peroxiredoxin-4 (Prx-IV) |
| Tumor necrosis factor ligand superfamily member 12 (Tweak) |
| Phosphoserine Aminotransferase (PSAT) |
| Glucagon-like Peptide 1, total (GLP-1 total) |
| Interleukin-15 (IL-15) |

Biomarkers that correlate with clinical assessments, including the Physician's Global Assessment, Patient's Global Assessment, and the HAQ quality of life score are shown in Table 12.

TABLE 12

| Biomarker |
|---|
| Cathepsin D |
| Pigment Epithelium Derived Factor (PEDF) |
| Serum Amyloid P-Component (SAP) |
| Sex Hormone-Binding Globulin (SHBG) |
| Alpha-1-Microglobulin (A1Micro) |
| Tissue type Plasminogen activator (tPA) |
| Alpha-1-acid glycoprotein 1 (AGP-1) |
| Chemerin |
| CD5 Antigen-like (CD5L) |
| FASLG Receptor (FAS) |
| C-Peptide |
| Phosphoserine Aminotransferase (PSAT) |
| Urokinase-type Plasminogen Activator (uPA) |
| Gastric inhibitory polypeptide (GIP) |
| Peroxiredoxin-4 (Prx-IV) |
| Hepatocyte Growth Factor (HGF) |
| Interleukin-15 (IL-15) |

In conclusion, this example identifies many biomarkers that correlate with different assessments of RA disease activity. The seven biomarkers that were identified across multiple disease activity measures include Cathepsin D, Serum Amyloid P-Component (SAP), Pigment Epithelium Derived Factor (PEDF), C-peptide, Tissue-type Plasminogen Activator ((tPA), Chemerin, and FASLG Receptor (FAS).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the invention as defined in the appended claims.

What is claimed is:

1. A method for treating a subject for rheumatoid arthritis (RA), the method comprising:

i) performing at least one immunoassay on a blood sample from the subject to generate a dataset comprising protein level data for at least seven protein markers of a set comprising Serum Amyloid P-component (SAP), Cathepsin D (CPSD), Chemerin (TIG2), alpha-1-Microglobulin (A1 M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), van Willebrand Factor (VWF), Apolipoprotein C-III (Apo C-III), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Anti-leukoproteinase (ALP), Thymus and activation regulated chemokine (TARC), Plasminogen Activator Inhibitor 1 (PAI-1), Interleukin-15 (IL-15), Ceruloplasmin (CP), Complement Factor H-Related Protein 1 (CFHR1), Protein DJ-1 (DJ-1), Alpha-Fetoprotein (AFP), Chemokine CC-4 (HCC-4), Ferritin (FRTN), Immunoglobulin A (IgA), thrombin-Activatable Fibrinolysis (TAFT), Cystatin-B (CSTB), Alpha-1-Antichymotrypsin (AACT), Pancreatic Polypeptide (PPP), HeatShock Protein 70 (HSP-70), Transferrin Receptor Protein (TFR1), Tamm-Horsfall Urinary Glycoprotein (THP), Tenascin-C(TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (GFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), and Monocyte Chemotactic Protein 1 (MCP-1), wherein the at least seven protein markers comprise TIG2, PEDF, CPSD, SAP, C-Peptide, tPA, and FAS;

ii) calculating a biomarker disease activity score (BDAS) for the subject by applying the protein level data alone or in combination with a clinical parameter or assessment to an interpretation function, wherein the BDAS provides a quantitative measure of RA disease activity in the subject; and identifying the subject having the BDAS that indicates a need for therapy; and iii) administering a therapy to the identified subject comprising one or more of:

administering a therapeutic compound selected from disease-modifying anti-rheumatic drugs (DMARDs), biologic DMARDs, non-steroidal anti-inflammatory drugs (NSAIDs), and corticosteroids; and administering bariatric surgical intervention.

2. The method of claim 1, wherein the at least seven protein markers comprise Tyk2, PEDF, CPSD, SAP, C-Peptide, tPA, and FAS, and one or more of A1M, SHBG, GDF-15, Hp, CD5L, AGP-1, CLU, CRP, CFH, RAGE, FGF-21, vWF, AACT, CSTB, ST2, TAFI, uPA, TN, Prx-IV, Tweak, PSAT, GLP-1 total, and IL-15.

3. The method of claim 1, wherein the at least seven protein markers comprise TIG2, PEDF, CPSD, SAP, C-Peptide, tPA, and FAS, and one or more of SHBG, A1M, AGP-1, CD5L, CRP, PSAT, uPA, GIP, Prx-IV, HGF, and IL-15.

4. A method for treating a subject for rheumatoid arthritis (RA), the method comprising:

i) performing at least one immunoassay on a blood sample from the subject to generate a dataset comprising protein level data for at least seven protein markers of a set comprising Serum Amyloid P-component (SAP), Cathepsin D (CPSD), Chemerin (TIG2), alpha-1-Microglobulin (A1 M), Haptoglobin (Hp), Pigment Epithelium Derived Factor (PEDF), Clusterin (CLU), Tissue type Plasminogen activator (tPA), C-reactive protein (CRP), Monocyte Chemotactic Protein 4 (MCP-4), Alpha-1-acid glycoprotein 1 (AGP-1), Connecting Peptide (C-Peptide), Complement Factor H (CFH), Pulmonary and Activation Regulated chemokine (PARC), growth-regulated alpha protein (GRO-alpha), Sex Hormone-Binding Globulin (SHBG), Matrix Metalloproteinase-7 (MMP-7), Growth/differentiation factor 15 (GDF-15), Fibroblast Growth Factor 21 (FGF-21), Angiopoietin-related protein 3 (ANGPTL3), Hemopexin (HPX), FASLG Receptor (FAS), Receptor for Advanced Glycosylation End products (RAGE), CD5 Antigen-like (CD5L), Endoglin (ENG), van Willebrand Factor (VWF), Apolipoprotein C-111 (Apo C-111), Interleukin-1 receptor antagonist (IL-1ra), Ficolin-3 (FCN3), Peroxiredoxin-4 (Prx-IV), ST2 cardiac biomarker (ST2), Sortilin (SORT1), Tumor necrosis factor ligand superfamily member 12 (Tweak), Phosphoserine Aminotrasferase (PSAT), Heparin-Binding EGF-Like Growth Factor (HB-EGF), Interleukin-8 (IL-8), Beta-2-Microglobulin (B2M), Apolipoprotein E (Apo E), Urokinase-type Plasminogen Activator (uPA), Adrenomedullin (ADM), Urokinase-type plasminogen, activator receptor (uPAR), Tetranectin (TN), E-Selectin (ESEL), Monokine Induced by Gamma Interferon (MIG), Glucagon-like Peptide 1, total (GLP-1 total), Interleukin-12 Subunit p40 (IL-12p40), Cartilage Oligomeric Matric protein (COMP), Apolipoprotein H (Apo H), Factor VII (F7), Interferon-inducible T-cell alpha chemoattractant (ITAC), Anti-leukoproteinase (ALP), Thymus and activation regulated chemokine (TARC), Plasminogen Activator Inhibitor 1 (PAI-1), Interleukin-15 (IL-15), Ceruloplasmin (CP), Complement Factor H-Related Protein 1 (CFHR1), Protein DJ-1 (DJ-1), Alpha-Fetoprotein (AFP), Chemokine CC-4 (HCC-4), Ferritin (FRTN), Immunoglobulin A (IgA), thrombin-Activatable Fibrinolysis (TAFT), Cystatin-B (CSTB), Alpha-1-Antichymotrypsin (AACT), Pancreatic Polypeptide (PPP), HeatShock Protein 70 (HSP-70), Transferrin Receptor Protein (TFR1), Tamm-Horsfall Urinary Glycoprotein (THP), Tenascin-C(TN-C), pepsinogen 1 (PG1), Hepatocyte Growth Factor (HGF), T-Cell-Specific Protein RANTES (RANTES), Tumor Necrosis Factor Receptor 2 (TNFR2), Macrophage Colony-Stimulating Factor 1 (M-CSF), Beta Amyloid 1-40 (AB-40), cystatin-C, Tissue Inhibitor of Metalloproteinases 3 (TIMP-3), Insulin-like Growth Factor binding Protein 4 (IGFBP4), Gastric Inhibitory Polypeptide (GIP), Midkine (MDK), Angiogenin (ANG), Stem Cell Factor (SCF), Myeloid Progenitor Inhibitory Factor 1 (MPIF-1), Osteoprotegerin (OPG), CD 40 antigen (CD40), Monocyte Chemotactic Protein 2 (MCP-2), Insulin-like Growth Factor-binding Protein 1 (GFBP-1), Vitamin K-Dependent Protein S (VKDPS), Hepatocyte Growth Factor Receptor (HGFR), Brain-Derived Neurotrophic Factor (BDNF), Macrophage-Stimulating Protein (MSP), and Monocyte Chemotactic Protein 1 (MCP-1), wherein the at least seven protein markers comprise TIG2, PEDF, CPSD, SAP, C-Peptide, tPA, and FAS;

ii) obtaining reference data from a reference group, the reference data comprising clinical assessment data for each member of the reference group and protein level data for each member of the reference group using the same markers as used for the subject, wherein the clinical assessment data comprises one or more of DAS28, DAS28-ESR, DAS28-CRP, health assessment questionnaire (HAQ), modified HAQ (mHAQ), multi-dimensional HAQ (MDHAQ), visual analog scale (VAS), physician global assessment VAS, patient global assessment VAS, pain VAS, fatigue VAS, overall VAS, sleep VAS, simplified disease activity index (SDAI), clinical disease activity index (CDAI), routine assessment of patient index data (RAPID), RAPID3, RAPID4, RAPIDS, American College of Rheumatology (ACR), ACR20, ACR50, ACR70, SF-36, RA MRI score (RAMRIS), total Sharp score (TSS), van der Heijde-modified TSS, van der Heijde modified Sharp score (SHS), Larsen score, TJC, swollen joint count (SJC), CRP titer, and erythrocyte sedimentation rate (ESR);

iii) applying a statistical tool to the reference data for determining a coefficient in an interpretation function for each of the protein level data;

iv) calculating a biomarker disease activity score (BDAS) for the subject by applying the protein level data from the subject to the interpretation function, wherein the BDAS provides a quantitative measure of RA disease activity in the subject; and identifying the subject having the BDAS that indicates a need for therapy; and v) administering a therapy to the identified subject comprising one or more of:

administering a therapeutic compound selected from disease-modifying anti-rheumatic drugs (DMARDs), biologic DMARDs, non-steroidal anti-inflammatory drugs (NSAIDs), and corticosteroids; and administering bariatric surgical intervention.

5. The method of claim 4, wherein the subject has one or more of RA radiographic progression, flare, or joint damage.

6. The method of claim 4, wherein the at least seven protein markers comprise TIG2, PEDF, CPSD, SAP, C-Peptide, tPA, and FAS, and one or more of A1M, SHBG, GDF-15, Hp, CD5L, AGP-1, CLU, CRP, CFH, RAGE, FGF-21, vWF, AACT, CSTB, ST2, TAFI, uPA, TN, Prx-IV, Tweak, PSAT, GLP-1 total, and IL-15.

7. The method of claim 4, wherein the at least seven protein markers comprise TIG2, PEDF, CPSD, SAP, C-Peptide, tPA, and FAS, one or more of SHBG, A1M, AGP-1, CD5L, CRP, PSAT, uPA, GIP, Prx-IV, HGF, and IL-15.

* * * * *